(12) United States Patent
Cragg

(10) Patent No.: US 7,744,599 B2
(45) Date of Patent: *Jun. 29, 2010

(54) ARTICULATING SPINAL IMPLANT

(75) Inventor: Andrew H. Cragg, Edina, MN (US)

(73) Assignee: TranS1 Inc., Wilmington, NC (US)

( * ) Notice: Subject to any disclaimer, the term of this patent is extended or adjusted under 35 U.S.C. 154(b) by 132 days.

This patent is subject to a terminal disclaimer.

(21) Appl. No.: 11/762,669

(22) Filed: Jun. 13, 2007

(65) Prior Publication Data

US 2007/0233260 A1 Oct. 4, 2007

Related U.S. Application Data

(63) Continuation of application No. 10/990,705, filed on Nov. 17, 2004, now Pat. No. 7,329,259, which is a continuation of application No. 10/125,771, filed on Apr. 18, 2002, now Pat. No. 6,899,716, which is a continuation-in-part of application No. 09/848,556, filed on May 3, 2001, now Pat. No. 7,014,633, which is a continuation-in-part of application No. 09/782,583, filed on Feb. 13, 2001, now Pat. No. 6,558,390.

(60) Provisional application No. 60/182,748, filed on Feb. 16, 2000.

(51) Int. Cl.
*A61B 17/56* (2006.01)

(52) U.S. Cl. ................ 606/86 R; 606/247; 128/898

(58) Field of Classification Search ................ 606/279, 606/86 R, 86 A, 247; 604/500, 506; 128/898
See application file for complete search history.

(56) References Cited

U.S. PATENT DOCUMENTS

| | | | |
|---|---|---|---|
| 1,630,239 A | 5/1927 | Binkley et al. | |
| 2,336,338 A | 12/1943 | Zublin | |
| 3,103,926 A | 9/1963 | Cochran et al. | |
| 3,367,326 A | * 2/1968 | Frazier | 606/86 A |
| 3,554,192 A | 1/1971 | Isberner | |
| 3,867,728 A | 2/1975 | Stubstad | |
| 3,875,595 A | 4/1975 | Froning | |
| 3,892,232 A | 7/1975 | Neufeld | |

(Continued)

FOREIGN PATENT DOCUMENTS

EP 0 611 116 B1 4/1994

(Continued)

OTHER PUBLICATIONS

U.S. Appl. No. 11/940,208, filed Nov. 14, 2007, Assell, et al.

(Continued)

*Primary Examiner*—Pedro Philogene
(74) *Attorney, Agent, or Firm*—Knobbe, Martens, Olson & Bear, LLP.

(57) ABSTRACT

Disclosed are methods and devices for accessing and treating the spine, while minimizing trauma to surrounding tissue. A device is introduced through tissue, to an access point on the spine. The device is thereafter advanced axially within the spine, from the access point across a treatment zone. In one embodiment, the device comprises an articulating spinal implant comprising a first elongate segment, a second elongate segment, and an articulating joint between the first and second segments.

17 Claims, 13 Drawing Sheets

U.S. PATENT DOCUMENTS

| | | |
|---|---|---|
| 4,135,506 A | 1/1979 | Ulrich |
| 4,170,990 A | 10/1979 | Baumgart et al. |
| 4,175,555 A | 11/1979 | Herbert |
| 4,265,231 A | 5/1981 | Scheller, Jr. et al. |
| 4,309,777 A | 1/1982 | Patil |
| 4,349,921 A | 9/1982 | Kuntz |
| 4,401,112 A | 8/1983 | Rezaian |
| 4,453,539 A | 6/1984 | Raftopoulos et al. |
| 4,541,423 A | 9/1985 | Barber |
| 4,545,374 A | 10/1985 | Jacobson |
| 4,553,273 A | 11/1985 | Wu |
| 4,554,914 A | 11/1985 | Kapp et al. |
| 4,573,448 A | 3/1986 | Kambin |
| 4,636,217 A | 1/1987 | Ogilvie et al. |
| 4,640,271 A | 2/1987 | Lower |
| 4,650,466 A | 3/1987 | Luther |
| 4,657,550 A | 4/1987 | Daher |
| 4,756,649 A | 7/1988 | Heule |
| 4,759,766 A | 7/1988 | Buettner-Janz et al. |
| 4,844,088 A | 7/1989 | Kambin |
| 4,858,601 A | 8/1989 | Glisson |
| 4,862,891 A | 9/1989 | Smith |
| 4,863,477 A | 9/1989 | Monson |
| 4,874,389 A | 10/1989 | Downey |
| 4,904,260 A | 2/1990 | Ray et al. |
| 4,911,718 A | 3/1990 | Lee et al. |
| 4,932,969 A | 6/1990 | Frey et al. |
| RE33,258 E | 7/1990 | Onik et al. |
| 4,946,378 A | 8/1990 | Hirayama et al. |
| RE33,348 E | 9/1990 | Lower |
| 4,966,604 A | 10/1990 | Reiss |
| 4,969,888 A | 11/1990 | Scholten et al. |
| 5,002,546 A | 3/1991 | Romano |
| 5,015,255 A | 5/1991 | Kuslich |
| 5,019,079 A | 5/1991 | Ross |
| 5,030,201 A | 7/1991 | Palestrant |
| 5,047,055 A | 9/1991 | Bao |
| 5,059,193 A | 10/1991 | Kuslich |
| 5,062,850 A | 11/1991 | MacMillan et al. |
| 5,071,437 A | 12/1991 | Steffee |
| 5,147,404 A | 9/1992 | Downey |
| 5,171,279 A | 12/1992 | Mathews |
| 5,171,280 A | 12/1992 | Baumgartner |
| 5,190,546 A | 3/1993 | Jervis |
| 5,192,326 A | 3/1993 | Bao et al. |
| 5,195,968 A | 3/1993 | Lundquist et al. |
| 5,236,460 A | 8/1993 | Barber |
| 5,242,443 A | 9/1993 | Kambin |
| 5,242,444 A | 9/1993 | MacMillan |
| 5,242,461 A | 9/1993 | Kortenbach et al. |
| 5,246,458 A | 9/1993 | Graham |
| 5,258,031 A | 11/1993 | Salib et al. |
| 5,269,785 A | 12/1993 | Bonutti |
| 5,285,795 A | 2/1994 | Ryan et al. |
| 5,290,289 A | 3/1994 | Sanders et al. |
| 5,313,962 A | 5/1994 | Obenchain |
| 5,336,223 A | 8/1994 | Rogers |
| 5,357,983 A | 10/1994 | Mathews |
| 5,360,448 A | 11/1994 | Thramann |
| 5,366,457 A | 11/1994 | McGuire et al. |
| 5,383,884 A | 1/1995 | Summers |
| 5,395,188 A | 3/1995 | Bailey et al. |
| 5,395,317 A | 3/1995 | Kambin |
| 5,396,880 A | 3/1995 | Kagan et al. |
| 5,403,276 A | 4/1995 | Schechter et al. |
| 5,415,661 A | 5/1995 | Holmes |
| 5,423,816 A | 6/1995 | Lin |
| 5,433,739 A * | 7/1995 | Sluijter et al. ................. 607/99 |
| 5,445,140 A | 8/1995 | Tovey |
| 5,458,642 A | 10/1995 | Beer et al. |
| 5,458,643 A | 10/1995 | Oka et al. |
| 5,480,440 A | 1/1996 | Kambin |
| 5,484,437 A | 1/1996 | Michelson |
| 5,489,308 A | 2/1996 | Kuslich et al. |
| 5,496,322 A | 3/1996 | Mathews |
| 5,505,732 A | 4/1996 | Michelson |
| 5,514,137 A | 5/1996 | Coutts |
| 5,514,180 A | 5/1996 | Heggeness et al. |
| 5,520,688 A | 5/1996 | Lin |
| 5,534,028 A | 7/1996 | Bao et al. |
| 5,534,031 A | 7/1996 | Matsuzaki et al. |
| 5,545,228 A | 8/1996 | Kambin |
| 5,545,229 A | 8/1996 | Parsons et al. |
| 5,549,679 A | 8/1996 | Kuslich |
| 5,554,163 A | 9/1996 | Shturman |
| 5,558,674 A | 9/1996 | Heggeness et al. |
| 5,562,736 A | 10/1996 | Ray et al. |
| 5,569,248 A | 10/1996 | Mathews |
| 5,571,189 A | 11/1996 | Kuslich |
| 5,571,190 A | 11/1996 | Ulrich et al. |
| 5,571,192 A | 11/1996 | Schonhoffer |
| 5,584,887 A | 12/1996 | Kambin |
| 5,591,170 A | 1/1997 | Spievack et al. |
| 5,630,816 A | 5/1997 | Kambin |
| 5,645,597 A | 7/1997 | Krapiva |
| 5,653,708 A | 8/1997 | Howland |
| 5,665,122 A | 9/1997 | Kambin |
| 5,669,909 A | 9/1997 | Zdeblick et al. |
| 5,674,294 A | 10/1997 | Bainville et al. |
| 5,674,295 A | 10/1997 | Ray et al. |
| 5,674,296 A | 10/1997 | Bryan et al. |
| 5,700,291 A | 12/1997 | Kuslich et al. |
| 5,702,449 A | 12/1997 | McKay |
| 5,702,453 A | 12/1997 | Rabbe et al. |
| 5,702,454 A | 12/1997 | Baumgartner |
| 5,702,455 A | 12/1997 | Saggar |
| 5,713,904 A | 2/1998 | Errico et al. |
| 5,728,097 A | 3/1998 | Mathews |
| 5,733,284 A | 3/1998 | Martin |
| 5,735,899 A | 4/1998 | Schwartz et al. |
| 5,741,253 A | 4/1998 | Michelson |
| 5,741,261 A | 4/1998 | Moskovitz et al. |
| 5,743,912 A | 4/1998 | Lahille et al. |
| 5,762,629 A | 6/1998 | Kambin |
| 5,779,704 A | 7/1998 | Kim |
| 5,785,709 A | 7/1998 | Kummer et al. |
| 5,792,044 A | 8/1998 | Foley et al. |
| 5,807,318 A | 9/1998 | St. Goar et al. |
| 5,824,093 A | 10/1998 | Ray et al. |
| 5,827,285 A | 10/1998 | Bramlet |
| 5,827,328 A | 10/1998 | Buttermann |
| 5,885,292 A | 3/1999 | Moskovitz et al. |
| 5,888,220 A | 3/1999 | Felt et al. |
| 5,888,223 A | 3/1999 | Bray, Jr. |
| 5,891,147 A | 4/1999 | Moskovitz et al. |
| 5,902,231 A | 5/1999 | Foley et al. |
| 5,906,616 A | 5/1999 | Pavlov et al. |
| 5,916,267 A | 6/1999 | Tienboon |
| 5,921,971 A | 7/1999 | Agro et al. |
| 5,928,239 A | 7/1999 | Mirza |
| 5,928,284 A | 7/1999 | Mehdizadeh |
| 5,935,131 A | 8/1999 | Bonutti |
| 5,954,635 A | 9/1999 | Foley et al. |
| 5,961,329 A | 10/1999 | Stucki-McCormick |
| 5,964,761 A | 10/1999 | Kambin |
| 5,968,062 A | 10/1999 | Thomas et al. |
| 5,972,015 A | 10/1999 | Scribner et al. |
| 5,976,146 A | 11/1999 | Ogawa et al. |
| 5,976,186 A | 11/1999 | Bao et al. |
| 5,976,187 A | 11/1999 | Richelsoph |
| 5,980,504 A | 11/1999 | Sharkey et al. |
| 5,989,256 A | 11/1999 | Kuslich et al. |
| 5,989,290 A | 11/1999 | Biedermann et al. |
| 6,001,101 A | 12/1999 | Augagneur et al. |

| | | | | | | |
|---|---|---|---|---|---|---|
| 6,001,130 A | 12/1999 | Bryan et al. | | 6,436,098 B1 | 8/2002 | Michelson |
| 6,007,487 A | 12/1999 | Foley et al. | | 6,436,102 B1 | 8/2002 | Ralph et al. |
| 6,010,495 A | 1/2000 | Tilton, Jr. | | 6,436,140 B1 | 8/2002 | Liu et al. |
| 6,010,502 A | 1/2000 | Bagby | | 6,436,143 B1 | 8/2002 | Ross et al. |
| 6,019,792 A | 2/2000 | Cauthen | | 6,440,138 B1 | 8/2002 | Reiley et al. |
| 6,022,362 A | 2/2000 | Lee et al. | | 6,443,988 B2 | 9/2002 | Felt et al. |
| 6,022,376 A | 2/2000 | Assell et al. | | 6,447,514 B1 | 9/2002 | Stalcup et al. |
| 6,030,162 A | 2/2000 | Huebner | | 6,447,518 B1 | 9/2002 | Krause et al. |
| 6,033,406 A | 3/2000 | Mathews | | 6,447,546 B1 | 9/2002 | Bramlet et al. |
| 6,036,696 A | 3/2000 | Lambrecht et al. | | 6,447,547 B1 | 9/2002 | Michelson |
| 6,053,916 A | 4/2000 | Moore | | 6,464,713 B2 | 10/2002 | Bonutti |
| 6,056,749 A * | 5/2000 | Kuslich ............... 606/86 A | | 6,482,234 B1 | 11/2002 | Weber et al. |
| 6,066,152 A | 5/2000 | Strauss et al. | | 6,482,235 B1 | 11/2002 | Lambrecht et al. |
| 6,066,154 A | 5/2000 | Reiley et al. | | 6,485,518 B1 | 11/2002 | Cornwall et al. |
| 6,080,099 A | 6/2000 | Slater et al. | | 6,500,173 B2 | 12/2002 | Underwood et al. |
| 6,086,589 A * | 7/2000 | Kuslich et al. ............ 606/247 | | 6,517,541 B1 | 2/2003 | Sesic |
| 6,093,205 A | 7/2000 | McLeod | | 6,533,791 B1 | 3/2003 | Betz et al. |
| 6,093,207 A | 7/2000 | Pisharodi | | 6,540,747 B1 | 4/2003 | Marino |
| 6,095,149 A | 8/2000 | Sharkey et al. | | 6,558,386 B1 | 5/2003 | Cragg |
| 6,110,210 A | 8/2000 | Norton et al. | | 6,558,390 B2 * | 5/2003 | Cragg ..................... 606/80 |
| RE36,857 E | 9/2000 | Euteneuer et al. | | 6,562,046 B2 | 5/2003 | Sasso |
| 6,120,502 A | 9/2000 | Michelson | | 6,575,979 B1 | 6/2003 | Cragg |
| 6,123,705 A | 9/2000 | Michelson | | 6,607,530 B1 | 8/2003 | Carl et al. |
| 6,127,597 A | 10/2000 | Beyar et al. | | 6,610,091 B1 | 8/2003 | Reiley |
| 6,132,465 A | 10/2000 | Ray et al. | | 6,652,535 B2 | 11/2003 | Kvarnstrom et al. |
| 6,140,452 A | 10/2000 | Felt et al. | | 6,692,495 B1 | 2/2004 | Zacouto |
| 6,152,871 A | 11/2000 | Foley et al. | | 6,719,797 B1 | 4/2004 | Ferree |
| 6,156,067 A | 12/2000 | Bryan et al. | | 6,740,090 B1 | 5/2004 | Cragg et al. |
| 6,159,212 A | 12/2000 | Schoedinger, III et al. | | 6,746,451 B2 | 6/2004 | Middleton et al. |
| 6,162,170 A | 12/2000 | Foley et al. | | 6,764,489 B2 | 7/2004 | Ferree |
| 6,175,758 B1 | 1/2001 | Kambin | | 6,790,210 B1 | 9/2004 | Cragg et al. |
| 6,176,823 B1 | 1/2001 | Foley et al. | | 6,805,697 B1 | 10/2004 | Helm et al. |
| 6,187,000 B1 | 2/2001 | Davison et al. | | 6,875,215 B2 | 4/2005 | Taras et al. |
| 6,187,043 B1 | 2/2001 | Ledergerber | | 6,899,716 B2 * | 5/2005 | Cragg ..................... 606/86 R |
| 6,187,048 B1 | 2/2001 | Milner et al. | | 6,921,403 B2 | 7/2005 | Cragg et al. |
| 6,206,822 B1 | 3/2001 | Foley et al. | | 6,991,653 B2 | 1/2006 | White et al. |
| 6,206,826 B1 | 3/2001 | Mathews et al. | | 7,014,633 B2 | 3/2006 | Cragg |
| 6,210,412 B1 | 4/2001 | Michelson | | 7,033,394 B2 | 4/2006 | Michelson |
| 6,217,509 B1 | 4/2001 | Foley et al. | | 7,037,309 B2 | 5/2006 | Weil et al. |
| 6,224,630 B1 | 5/2001 | Boa et al. | | 7,087,056 B2 | 8/2006 | Vaughan |
| 6,231,609 B1 | 5/2001 | Mehdizdeh | | 7,087,058 B2 | 8/2006 | Cragg |
| 6,240,926 B1 | 6/2001 | Chin Gan et al. | | 7,175,626 B2 | 2/2007 | Neff |
| 6,241,734 B1 | 6/2001 | Scribner et al. | | 7,309,338 B2 | 12/2007 | Cragg |
| 6,264,656 B1 | 7/2001 | Michelson | | 7,329,259 B2 | 2/2008 | Cragg |
| 6,264,695 B1 | 7/2001 | Stoy | | 7,473,256 B2 | 1/2009 | Assell et al. |
| 6,280,191 B1 | 8/2001 | Gordon | | 7,491,236 B2 | 2/2009 | Cragg et al. |
| 6,280,475 B1 | 8/2001 | Bao et al. | | 7,500,977 B2 | 3/2009 | Assell et al. |
| 6,287,313 B1 | 9/2001 | Sasso | | 7,530,993 B2 | 5/2009 | Assell et al. |
| 6,306,140 B1 | 10/2001 | Siddiqui | | 7,547,317 B2 | 6/2009 | Cragg |
| 6,306,143 B1 | 10/2001 | Kvarnstrom et al. | | 7,547,324 B2 | 6/2009 | Cragg et al. |
| 6,315,795 B1 | 11/2001 | Scarborough et al. | | 7,569,056 B2 | 8/2009 | Cragg et al. |
| 6,319,254 B1 | 11/2001 | Giet et al. | | 7,588,574 B2 | 9/2009 | Assell et al. |
| 6,348,055 B1 | 2/2002 | Preissman | | 7,608,077 B2 | 10/2009 | Cragg |
| 6,520,992 B1 | 2/2002 | Zollner et al. | | 2001/0004710 A1 | 6/2001 | Felt et al. |
| 6,371,968 B1 | 4/2002 | Kogasaka et al. | | 2002/0022888 A1 | 2/2002 | Serhan et al. |
| 6,371,990 B1 | 4/2002 | Ferree | | 2002/0026244 A1 | 2/2002 | Trieu |
| 6,375,682 B1 | 4/2002 | Fleischmann et al. | | 2002/0032444 A1 | 3/2002 | Mische |
| 6,379,334 B1 | 4/2002 | Frassica | | 2002/0032447 A1 | 3/2002 | Weikel et al. |
| 6,383,188 B2 | 5/2002 | Kuslich et al. | | 2002/0038123 A1 | 3/2002 | Visotsky et al. |
| 6,383,190 B1 | 5/2002 | Preissman | | 2002/0052608 A1 | 5/2002 | Kvarnstrom et al. |
| 6,387,130 B1 | 5/2002 | Stone et al. | | 2002/0055745 A1 | 5/2002 | Mckinley et al. |
| 6,395,007 B1 | 5/2002 | Bhatnagar et al. | | 2002/0068939 A1 | 6/2002 | Levy et al. |
| 6,395,032 B1 | 5/2002 | Gauchet | | 2002/0068974 A1 | 6/2002 | Kuslich et al. |
| 6,395,034 B1 | 5/2002 | Suddaby | | 2002/0072801 A1 | 6/2002 | Michelson |
| 6,402,750 B1 | 6/2002 | Atkinson et al. | | 2002/0077632 A1 | 6/2002 | Tsou |
| 6,402,784 B1 | 6/2002 | Wardlaw | | 2002/0077700 A1 | 6/2002 | Varga et al. |
| 6,409,766 B1 | 6/2002 | Brett | | 2002/0077702 A1 | 6/2002 | Castro |
| 6,416,515 B1 | 7/2002 | Wagner | | 2002/0082598 A1 | 6/2002 | Teitelbaum |
| 6,419,677 B2 | 7/2002 | Zuckerman et al. | | 2002/0082699 A1 | 6/2002 | Ward et al. |
| 6,419,678 B1 | 7/2002 | Asfora | | 2002/0087163 A1 | 7/2002 | Dixon et al. |
| 6,419,704 B1 | 7/2002 | Ferree | | 2002/0107573 A1 | 8/2002 | Steinberg |
| 6,423,095 B1 | 7/2002 | Van Hoeck et al. | | 2002/0110439 A1 | 8/2002 | Craven |
| 6,428,576 B1 | 8/2002 | Haldimann | | 2002/0123807 A1 | 9/2002 | Cauthen, III |

| | | |
|---|---|---|
| 2002/0128714 A1 | 9/2002 | Manasas et al. |
| 2002/0147485 A1 | 10/2002 | Mamo et al. |
| 2002/0147496 A1 | 10/2002 | Belef et al. |
| 2002/0147497 A1 | 10/2002 | Belef et al. |
| 2002/0151979 A1 | 10/2002 | Lambrecht et al. |
| 2002/0151980 A1 | 10/2002 | Cauthen, III |
| 2002/0156528 A1 | 10/2002 | Gau |
| 2002/0156531 A1 | 10/2002 | Felt et al. |
| 2002/0165542 A1 | 11/2002 | Ferree |
| 2002/0173851 A1 | 11/2002 | Mckay |
| 2002/0188292 A1 | 12/2002 | Sharkey et al. |
| 2003/0004574 A1 | 1/2003 | Ferree |
| 2003/0009296 A1 | 1/2003 | Graf |
| 2003/0023311 A1 | 1/2003 | Trieu |
| 2003/0028193 A1 | 2/2003 | Weil et al. |
| 2003/0033017 A1 | 2/2003 | Lotz et al. |
| 2003/0045881 A1 | 3/2003 | Barouk et al. |
| 2003/0065394 A1 | 4/2003 | Michelson |
| 2003/0130664 A1 | 7/2003 | Boucher et al. |
| 2003/0176926 A1 | 9/2003 | Boehm et al. |
| 2003/0181982 A1 | 9/2003 | Kuslich |
| 2003/0191474 A1 | 10/2003 | Cragg et al. |
| 2003/0195518 A1 | 10/2003 | Cragg |
| 2003/0195628 A1 | 10/2003 | Boa et al. |
| 2003/0195630 A1 | 10/2003 | Ferree |
| 2003/0204189 A1 | 10/2003 | Cragg |
| 2003/0212400 A1 | 11/2003 | Bloemer et al. |
| 2003/0220643 A1 | 11/2003 | Ferree |
| 2003/0220649 A1 | 11/2003 | Bao et al. |
| 2004/0002708 A1 | 1/2004 | Ritland |
| 2004/0010317 A1 | 1/2004 | Lambrecht et al. |
| 2004/0024465 A1 | 2/2004 | Lambrecht et al. |
| 2004/0030392 A1 | 2/2004 | Lambrecht et al. |
| 2004/0034429 A1 | 2/2004 | Lambrecht et al. |
| 2004/0138752 A1 | 7/2004 | Michelson |
| 2004/0141827 A1 | 7/2004 | Dicke |
| 2004/0151559 A1 | 8/2004 | Craven |
| 2004/0193155 A1 | 9/2004 | Castaneda |
| 2004/0220577 A1 | 11/2004 | Cragg et al. |
| 2004/0230195 A1 | 11/2004 | Kaikkonen et al. |
| 2005/0038438 A1 | 2/2005 | Anderson et al. |
| 2005/0101961 A1 | 5/2005 | Huebner et al. |
| 2005/0107791 A1 | 5/2005 | Manderson |
| 2005/0113919 A1 | 5/2005 | Cragg et al. |
| 2005/0113928 A1 | 5/2005 | Cragg et al. |
| 2005/0113929 A1 | 5/2005 | Cragg et al. |
| 2005/0149191 A1 | 7/2005 | Cragg et al. |
| 2006/0058800 A1 | 3/2006 | Ainsworth et al. |
| 2006/0079898 A1 | 4/2006 | Ainsworth et al. |
| 2006/0155297 A1 | 7/2006 | Ainsworth et al. |
| 2006/0206208 A1 | 9/2006 | Michelson |
| 2006/0206209 A1 | 9/2006 | Cragg et al. |
| 2006/0229622 A1 | 10/2006 | Huebner et al. |
| 2007/0010819 A1 | 1/2007 | Johnstone |
| 2007/0055260 A1 | 3/2007 | Cragg |
| 2007/0066977 A1 | 3/2007 | Assell et al. |
| 2007/0112351 A1 | 5/2007 | Assell et al. |
| 2007/0118132 A1 | 5/2007 | Culbert et al. |
| 2007/0167951 A1 | 7/2007 | Ainsworth et al. |
| 2007/0168036 A1 | 7/2007 | Ainsworth et al. |
| 2007/0260270 A1 | 11/2007 | Assell et al. |
| 2007/0265652 A1 | 11/2007 | Assell |
| 2008/0004707 A1 | 1/2008 | Cragg |
| 2008/0065076 A1 | 3/2008 | Cragg |
| 2008/0065080 A1 | 3/2008 | Assell et al. |
| 2008/0065092 A1 | 3/2008 | Assell et al. |
| 2008/0065093 A1 | 3/2008 | Assell et al. |
| 2008/0065094 A1 | 3/2008 | Assell et al. |
| 2008/0071278 A1 | 3/2008 | Assell et al. |
| 2008/0071282 A1 | 3/2008 | Assell et al. |
| 2008/0097452 A1 | 4/2008 | Assell et al. |
| 2008/0154275 A1 | 6/2008 | Assell et al. |
| 2008/0188895 A1 | 8/2008 | Cragg |
| 2008/0262502 A1 | 10/2008 | Ainsworth et al. |
| 2008/0262555 A1 | 10/2008 | Assell |
| 2009/0240293 A1 | 9/2009 | Cragg |
| 2009/0270902 A1 | 10/2009 | Assell et al. |

FOREIGN PATENT DOCUMENTS

| | | |
|---|---|---|
| EP | 0 980 677 A1 | 2/2000 |
| EP | 1 029 519 | 8/2000 |
| WO | WO 95/22285 | 8/1995 |
| WO | WO 97/40878 | 11/1997 |
| WO | WO 98/38918 | 9/1998 |
| WO | WO 99/47055 | 9/1999 |
| WO | WO 00/67650 | 11/2000 |
| WO | WO 01/28468 A1 | 4/2001 |
| WO | WO 01/60268 A1 | 8/2001 |
| WO | WO 02/09801 A1 | 2/2002 |
| WO | WO 02/13732 A2 | 2/2002 |
| WO | WO 02/34120 A2 | 5/2002 |
| WO | WO 02/058599 A2 | 8/2002 |
| WO | WO 02/071921 A2 | 9/2002 |

OTHER PUBLICATIONS

U.S. Appl. No. 11/940,252, filed Nov. 14, 2007, Assell, et al.
U.S. Appl. No. 11/940,265, filed Nov. 14, 2007, Assell, et al.
U.S. Appl. No. 11/942,470, filed Nov. 19, 2007, Assell, et al.
U.S. Appl. No. 11/942,488, filed Nov. 19, 2007, Assell, et al.
U.S. Appl. No. 11/942,547, filed Nov. 19, 2007, Assell, et al.
U.S. Appl. No. 11/953,724, filed Dec. 10, 2007, Assell, et al.
U.S. Appl. No. 11/956,236, filed Dec. 13, 2007, Cragg.
U.S. Appl. No. 12/046,335, filed Mar. 11, 2008, Assell, et al.
U.S. Appl. No. 11/762,646, filed Jun. 13, 2007, Cragg.
J.J. Trambert, M.D., "Percutaneous Interventions in the Presacral Space: CT-guided Precoccygeal Approach—Early Experience," (Radiology 1999; 213:901-904).
R. Johnsson, et al., "Posterolateral Lumbar Fusion Using Facet Joint Fixation With Biodegradable Rods: A Pilot Study," Eur Spine J., (1997) 6:144-148.
R.P. Louis, M.D., "Anatomy, Physiology, and Biomechanics of the Lumbopelvic Junction," Lumbosacral and Spinopelvic Fusion, Chapter 1 (pp. 1-11) Lippincott-Raven Publishers (1996).
M.R. Zindrick, M.D., et al., "Clinical Anatomy of the Lumbosacral Junction and Pelvix," Lumbosacral and Spinopelvic Fusion, Chapter 2 (pp. 13-25) Lippincott-Raven Publishers (1996).
J.W. Olgilvie, M.D., et al., "Overview of Fixation to the Sacrum & Pelvis in Spinal Surgery," Lumbosacral and Spinopelvic Fusion, Chapter 17 (pp. 191-198) Lippincott-Raven Publishers (1996).
S.A. Caruso, M.E., et al., "Instrumented Fusions of the Lumbosacral Spine: A Technical Overview," Lumbosacral and Spinopelvic Fusion, Chapter 18 (pp. 199-210) Lippincott-Raven Publishers (1996).
R.P. Louis, M.D., "Lumbopelvic Fusion," Lumbosacral and Spinopelvic Fusion, Chapter 38, (pp. 479-492) Lippincott-Raven Publishers (1996).
J. Dove, FRCS, "The Hartshill System for the Front of the Lumbosacral Spine," Lumbosacral and Spinopelvic Fusion, Chapter 42 (pp. 539-543) Lippincott-Raven Publishers (1996).
P. Kambin, M.D., et al., "Arthroscopic fusion of the Lumbosacral Spine," Lumbosacral and Spinopelvic Fusion, Chapter 44 (pp. 565-577) Lippincott-Raven Publishers (1996).
B. Jeanneret, et al., "Posterior Stabilization in L5-S1 Isthmic Spondylolisthesis with Paralaminar Screw Fixation: Anatomical and Clinical Results," Journal ofSpinal Disorders, vol. 9, No. 3, pp. 223-233 (1996) Lippincott-Raven Publishers, Philadelphia.
Jason A. Smith, MD, et al., "Clinical Outcome of Trans-Sacral Interbody Fusion After Partial Reduction for High-Grade L5-S1 Spondylolisthesis," Spine, 2001, vol. 26, No. 20, pp. 2227-2234.
Michael MacMillan, MD, et al., "Percutaneous Lumbosacral Fixation and Fusion," Percutaneous Spine Techniques, Jan. 1996, vol. 7, No. 1, pp. 99-106.
Curtis A. Dickman, M.D., et al., "Transpedicular screw-rod fixation of the lumbar spine: operative technique and outcome in 104 cases," J. Neurosurg, Dec. 1992, vol. 77, pp. 860-870.

Richard M. Slone, MD, et al., "Spinal Fixation, Part 1, Basic Hardware, and Fixation Techniques for the Cervical Spine," RadioGraphics, 1993, vol. 13, No. 2, pp. 341-356.

Richard M. Slone, MD, et al., "Spinal Fixation, Part 2, Fixation Techniques and Hardware for the Thoracic and Lumbosacral Spine," RadioGraphics, 1993, vol. 13, No. 3, pp. 521-543.

Michael MacMillan, et al., Biomechanical Analysis of a New Anterior Spine Implant for Post-Corpectomy Instability, Journal of Spinal Disorders, 1995, vol. 8, No. 1, pp. 56-61.

Hallett H. Mathews, M.D., "Minimally Invasive Fusion Techniques, Percutaneous Interbody Fusions," Orthopedic Clinics of North America, Oct. 1998, vol. 29, No. 4.

Parviz Kambin, M.D., et al., "Arthroscopic Microdiscectomy: An Alternative to Open Disc Surgery," The Mount Sinai Journal of Medicine, Sep. 2000, vol. 67, No. 4.

Hallett H. Mathews, M.D., et al., "Perspectives on Modern Orthopaedics, Minimally Invasive Techniques for the Treatment of Intervertebral Disk Herniation," Journal of the American Academy of Orthopaedic Surgeons, Mar./Apr. 2002, vol. 10, No. 2.

Parviz Kambin, M.D., "Percutaneous Spine Techniques, Diagnostic and Therapeutic Spinal Arthroscopy," Neurosurgery Clinics of North America, Jan. 1996, vol. 7, No. 1.

Parviz Kambin, M.D., et al., "Arthroscopic Discectomy of the Lumbar Spine," Clinical Orthopaedics and Related Research, Apr. 1997, No. 337.

John L. Emmett, M.D., M.S. (Urology), David M. Witten, M.D., M.S. (Radiology)—vol. 1, Third Edition—Clinical Urography—An Atlas and Textbook of Roentgenologic Diagnosis—1971—Phneumography (Retroperitoneal Gas [Air] Insufflation; Perirenal Insufflation; Presacral Insufflation).

Friedrich W. Rathke and Karl F. Schlegel, Surgery of the Spine, Atlas of Orthopaedic Operations, vol. 1, 1979, pp. 222-224.

* cited by examiner

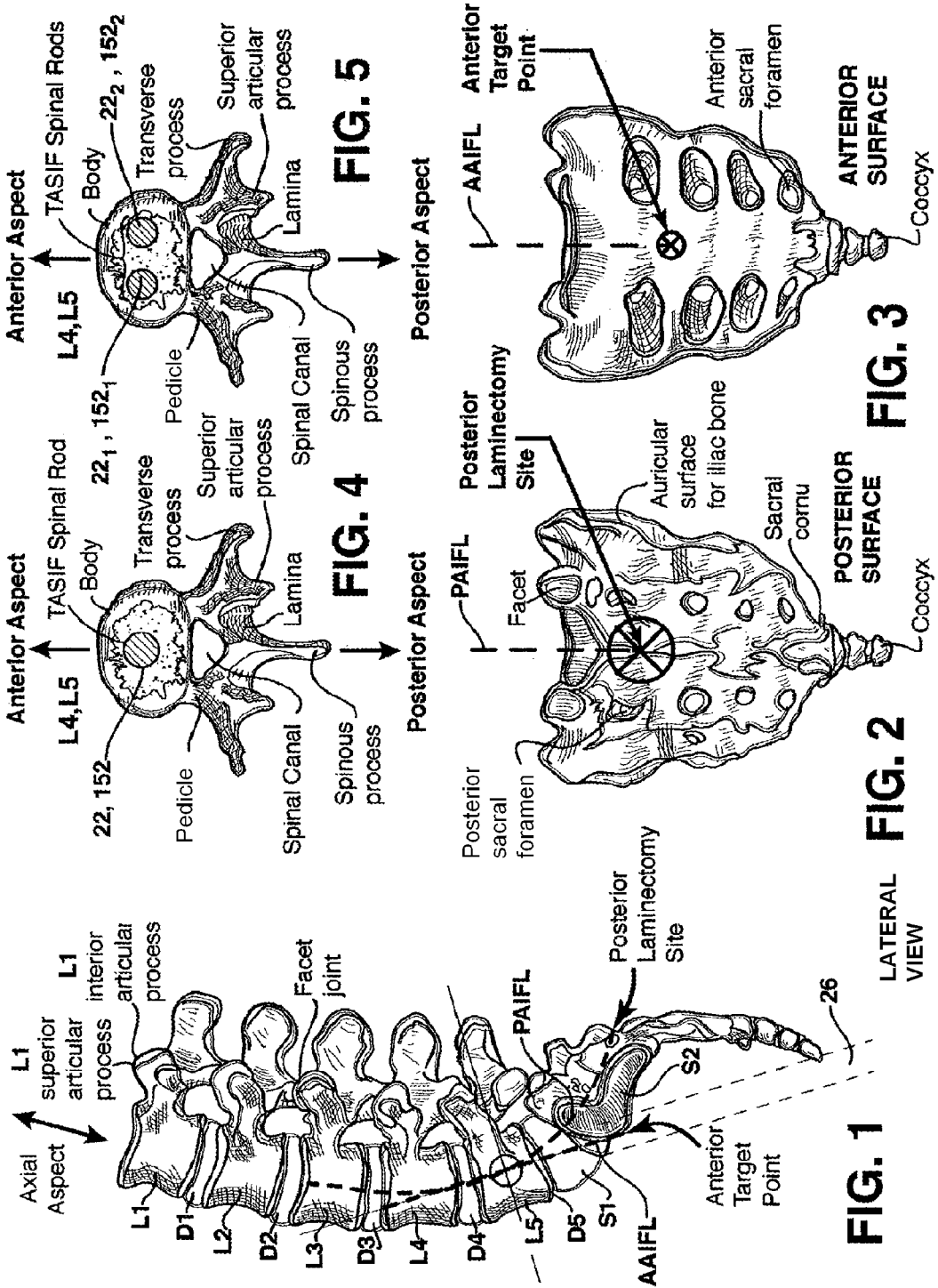

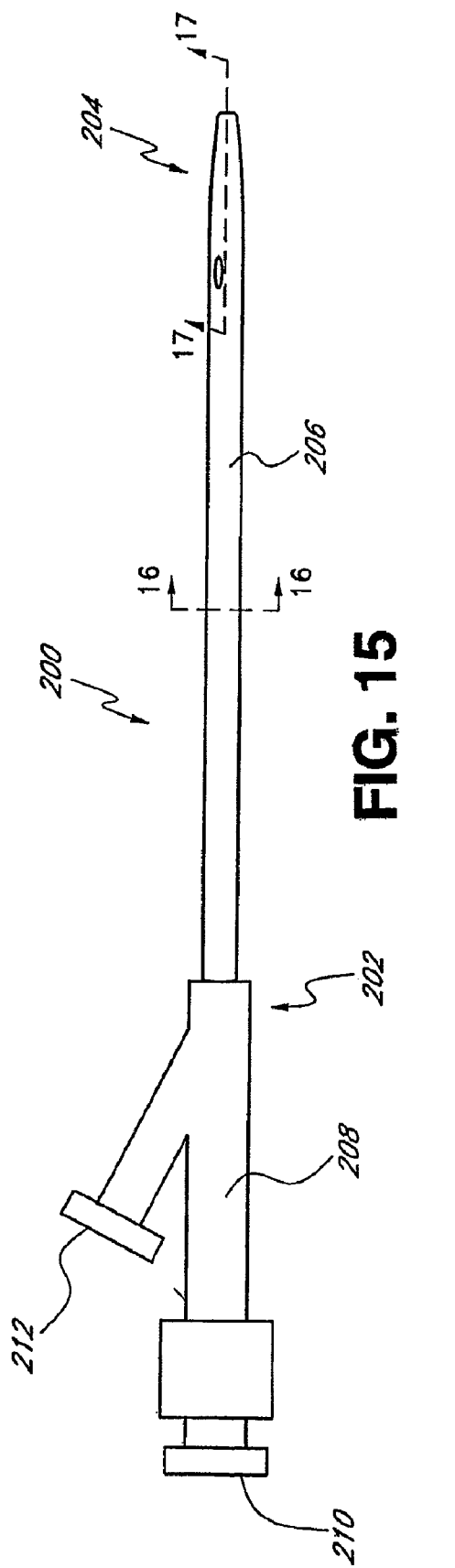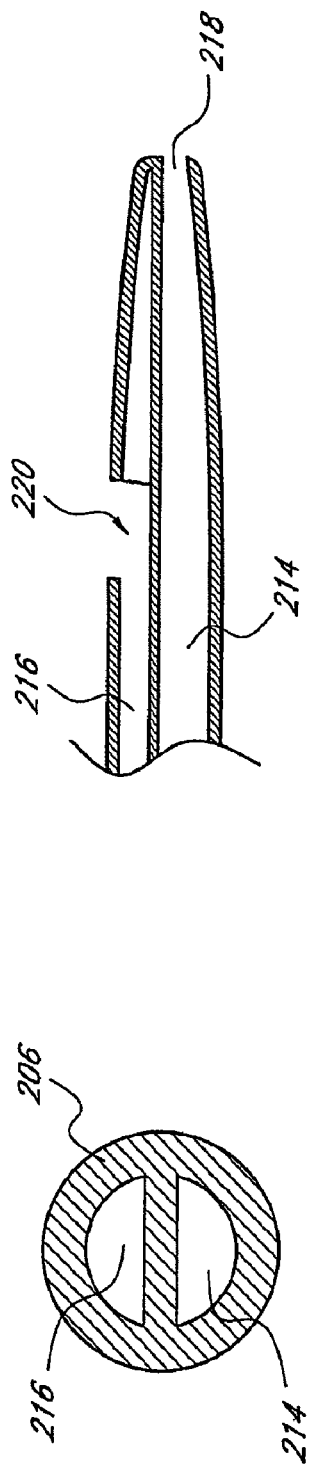
FIG. 15
FIG. 16
FIG. 17

ARTICULATING SPINAL IMPLANT

CROSS-REFERENCE TO RELATED APPLICATIONS

This application is a continuation of U.S. patent application Ser. No. 10/990,705, filed Nov. 17, 2004, which is a continuation of U.S. patent application Ser. No. 10/125,771, filed Apr. 18, 2002 and issued as U.S. Pat. No. 6,899,716 on May 31, 2005, which is a continuation-in-part of U.S. patent application Ser. No. 09/848,556, filed May 3, 2001 and issued as U.S. Pat. No. 7,014,633 on Mar. 21, 2006, which is a continuation-in-part of U.S. patent application Ser. No. 09/782,583, filed Feb. 13, 2001 and issued as U.S. Pat. No. 6,558,390 on May 6, 2003, which claims priority to U.S. Provisional Patent Application No. 60/182,748, filed Feb. 16, 2000, the contents of each of which are incorporated in their entirety into this disclosure by reference.

BACKGROUND OF THE INVENTION

1. Field of the Invention

The present invention relates generally to spinal surgery, particularly methods and apparatus for forming one or more trans-sacral axial spinal instrumentation/fusion (TASIF) axial bore through vertebral bodies in general alignment with a visualized, trans-sacral anterior or posterior axial instrumentation/fusion line (AAIFL or PAIFL) in a minimally invasive, low trauma, manner and providing a therapy to the spine employing the axial bore.

It has been estimated that 70% of adults have had a significant episode of back pain or chronic back pain emanating from a region of the spinal column or backbone. Many people suffering chronic back pain or an injury requiring immediate intervention resort to surgical intervention to alleviate their pain.

The spinal column or backbone encloses the spinal cord and consists of 33 vertebrae superimposed upon one another in a series which provides a flexible supporting column for the trunk and head. The vertebrae cephalad (i.e., toward the head or superior) to the sacral vertebrae are separated by fibrocartilaginous intervertebral discs and are united by articular capsules and by ligaments. The uppermost seven vertebrae are referred to as the cervical vertebrae, and the next lower twelve vertebrae are referred to as the thoracic, or dorsal, vertebrae. The next lower succeeding five vertebrae below the thoracic vertebrae are referred to as the lumbar vertebrae and are designated L1-L5 in descending order. The next lower succeeding five vertebrae below the lumbar vertebrae are referred to as the sacral vertebrae and are numbered S1-S5 in descending order. The final four vertebrae below the sacral vertebrae are referred to as the coccygeal vertebrae. In adults, the five sacral vertebrae fuse to form a single bone referred to as the sacrum, and the four rudimentary coccyx vertebrae fuse to form another bone called the coccyx or commonly the "tail bone". The number of vertebrae is sometimes increased by an additional vertebra in one region, and sometimes one may be absent in another region.

Typical lumbar, thoracic and cervical vertebrae consist of a ventral or vertebral body and a dorsal or neural arch. In the thoracic region, the ventral body bears two costal pits for reception of the head of a rib on each side. The arch which encloses the vertebral foramen is formed of two pedicles and two lamina. A pedicle is the bony process which projects backward or anteriorly from the body of a vertebra connecting with the lamina on each side. The pedicle forms the root of the vertebral arch. The vertebral arch bears seven processes: a dorsal spinous process, two lateral transverse processes, and four articular processes (two superior and two inferior). A deep concavity, inferior vertebral notch, on the inferior border of the arch provides a passageway or spinal canal for the delicate spinal cord and nerves. The successive vertebral foramina surround the spinal cord. Articulating processes of the vertebrae extend posteriorly of the spinal canal.

The bodies of successive lumbar, thoracic and cervical vertebrae articulate with one another and are separated by the intervertebral spinal discs. Each spinal disc comprises a fibrous cartilage shell enclosing a central mass, the "nucleus pulposus" (or "nucleus" herein) that provides for cushioning and dampening of compressive forces to the spinal column. The shell enclosing the nucleus comprises cartilaginous endplates adhered to the opposed cortical bone endplates of the cephalad and caudal vertebral bodies and the "annulus fibrosis" (or "annulus" herein) comprising an annular fibrosis layer of collagen fibers running circumferentially around the nucleus pulposus and connecting the cartilaginous endplates. The nucleus contains hydrophilic (water attracting) micropolysacharides and fibrous strands. The nucleus is relatively inelastic, but the annulus can bulge outward slightly to accommodate loads axially applied to the spinal motion segment.

The intervertebral discs are anterior to the spinal canal and located between the opposed end faces or endplates of a cephalad and a caudal vertebral body. The inferior articular processes articulate with the superior articular processes of the next succeeding vertebra in the caudal (i.e., toward the feet or inferior) direction. Several ligaments (supraspinous, interspinous, anterior and posterior longitudinal, and the ligamenta flava) hold the vertebrae in position yet permit a limited degree of movement. The assembly of two vertebral bodies, the interposed, intervertebral, spinal disc and the attached ligaments, muscles and facet joints is referred to as a "spinal motion segment".

The relatively large vertebral bodies located in the anterior portion of the spine and the intervertebral discs provide the majority of the weight bearing support of the vertebral column. Each vertebral body has relatively strong, cortical bone layer comprising the exposed outside surface of the body, including the endplates, and weak, cancellous bone comprising the center of the vertebral body.

A number of spinal disorders are caused by traumatic spinal injuries, disease processes, aging processes, and congenital abnormalities that cause pain, reduce the flexibility of the spine, decrease the load bearing capability of the spine, shorten the length of the spine, and/or distort the normal curvature of the spine. These spinal disorders and various treatments that have been clinically used or proposed are first described as follows.

With aging, the nucleus becomes less fluid and more viscous and sometimes even dehydrates and contracts (sometimes referred to as "isolated disc resorption") causing severe pain in many instances. In addition, the annulus tends to thicken, desiccate, and become more rigid, lessening its ability to elastically deform under load and making it susceptible to fracturing or fissuring.

One form of degeneration of the disc occurs when the annulus fissures or is rent. The fissure may or may not be accompanied by extrusion of nucleus material into and beyond the annulus. The fissure itself may be the sole morphological change, above and beyond generalized degenerative changes in the connective tissue of the disc, and disc fissures can nevertheless be painful and debilitating. Biochemicals contained within the nucleus are allowed to escape through the fissure and irritate nearby structures.

A fissure also may be associated with a herniation or rupture of the annulus causing the nucleus to bulge outward or extrude out through the fissure and impinge upon the spinal column or nerves (a "ruptured" or "slipped" disc). With a contained disc herniation, the nucleus may work its way partly through the annulus but is still contained within the annulus or beneath the posterior longitudinal ligament, and there are no free nucleus fragments in the spinal canal. Nevertheless, even a contained disc herniation is problematic because the outward protrusion can press on the spinal cord or on spinal nerves causing sciatica.

Another disc problem occurs when the disc bulges outward circumferentially in all directions and not just in one location. This occurs when over time, the disc weakens, bulges outward and takes on a "roll" shape. Mechanical stiffness of the joint is reduced and the spinal motion segment may become unstable shortening the spinal cord segment. As the disc "roll" extends beyond the normal circumference, the disc height may be compromised, and foramina with nerve roots are compressed causing pain. In addition, osteophytes may form on the outer surface of the disc roll and further encroach on the spinal canal and foramina through which nerves pass. The cephalad vertebra may eventually settle on top of the caudal vertebra. This condition is called "lumbar spondylosis".

In addition, various types of spinal column displacement disorders are known in one or more spinal motion segment that are hereditary or are caused by degenerative disease processes or trauma. Such spinal displacement disorders include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in the lumbar or cervical spine). At times the displacement disorder is accompanied by or caused by a fracture or partial collapse of one or more vertebrae or degeneration of a disc. Patients who suffer from such conditions can experience moderate to severe distortion of the thoracic skeletal structure, diminished ability to bear loads, loss of mobility, extreme and debilitating pain, and oftentimes suffer neurologic deficit in nerve function.

Approximately 95% of spinal surgery involves the lower lumbar vertebrae designated as the fourth lumbar vertebra ("L4"), the fifth lumbar vertebra ("L5"), and the first sacral vertebra ("S1"). Persistent low back pain is attributed primarily to degeneration of the disc connecting L5 and S1. Traditional, conservative methods of treatment include bed rest, pain and muscle relaxant medication, physical therapy or steroid injection. Upon failure of conservative therapy spinal pain (assumed to be due to instability) has traditionally been treated by spinal fusion, with or without instrumentation, which causes the vertebrae above and below the disc to grow solidly together and form a single, solid piece of bone.

2. Description of the Related Art

Highly invasive, open surgical procedures have been developed and used to perform a "complete discectomy" to surgically remove the disc, and the vertebral bodies are then fused together. The removal of the disc involves removing the nucleus, cutting away the cartilaginous endplates adhered to the opposed cortical bone endplates of the cephalad and caudal vertebral bodies, and removing at least a portion of the annulus. Fusion of the vertebral bodies involves preparation of the exposed endplate surfaces by decortication (scraping the endplate cortical bone) and the deposition of additional bone into disc space between the prepared endplate surfaces. The complete discectomy and fusion may be performed through a posterior surgical route (from the back side of the patient) or an anterior surgical route (from the front side of the patient). The removed vertebral bone may be just the hard cortical bone or may include soft cancellous soft bone in the interior of the vertebral bodies. Controversy exists regarding the preferred method of performing these fusions for various conditions of the spine. Sometimes, non-biological materials are used to augment and support the bone grail (fixation systems). Sometimes, the fixation is performed from the posterior route (posterior fixation), or from the anterior route (anterior fixation), or even both sides (anterior-posterior fixations or circumferential fusion).

Current treatment methods other than spinal fusion for symptomatic disc rolls and herniated discs include "laminectomy" which involves the lateral surgical exposure of the annulus and surgical excision of the symptomatic portion of the herniated disc followed by a relatively lengthy recuperation period.

Various other surgical treatments that attempt to preserve the intervertebral spinal disc and to simply relieve pain include a "nucleotomy" or "disc decompression" to remove some or most of the interior nucleus thereby decompressing and decreasing outward pressure on the annulus. In less invasive microsurgical procedures known as "microlumbar discectomy" and "automated percutaneous lumbar discectomy", the nucleus is removed by suction through a needle laterally extended through the annulus. Although these procedures are less invasive than open surgery, they nevertheless suffer the possibility of injury to the nerve root and dural sac, perineural scar formation, reherniation of the site of the surgery, and instability due to excess bone removal. Moreover, they involve the perforation of the annulus.

Another method of treatment is known as "chemonucleolysis", which is carried out by injection of the enzyme chymopapain into the nucleus through the annulus. This procedure has many complications including severe pain and spasm, which may last up to several weeks following injection. Sensitivity reactions and anaphylactic shock occur in limited but significant numbers of patients.

Although damaged discs and vertebral bodies can be identified with sophisticated diagnostic imaging, the surgical procedures are so extensive that clinical outcomes are not consistently satisfactory. Furthermore, patients undergoing such fusion surgery experience significant complications and uncomfortable, prolonged convalescence. Surgical complications include disc space infection, nerve root injury, hematoma formation, and instability of adjacent vertebrae.

Many surgical techniques, instruments and spinal disc implants have been described in the medical literature and in patents that are directed to providing less invasive, percutaneous, lateral access to a degenerated intervertebral spinal disc. Then, instruments are introduced through lateral disc openings made through the annulus for performing a discectomy and implanting bone growth materials or biomaterials or spinal disc implants inside the annulus. Or, one or more laterally extending space or hole is bored through the disc to receive one or more laterally inserted spinal disc implant or bone growth material to promote fusion or to receive a preformed, artificial, functional disc replacement implant as typified by U.S. Pat. No. 5,700,291.

Percutaneous lateral procedures and instruments for performing such discectomies are disclosed in U.S. Pat. No. Re. 33,258, U.S. Pat. Nos. 4,573,448, 5,015,255, 5,313,962, 5,383,884, 5,702,454, 5,762,629, 5,976,146, 6,095,149, and 6,127,597 and in PCT publication WO 99/47055, for example. A laparascopic technique and apparatus for traversing the retroperitoneal space from an abdominal skin incision to an anterior surface of the disc annulus and performing a discoscopy is disclosed in the '962 patent, for example. Percutaneous surgical disc procedures and apparatus that accesses the disc in a posterolateral approach from a skin incision in the patient's back are described in the '629 and '448 patents, for example.

The nucleus is fragmented by various mechanical cutting heads as disclosed, for example in the '258, '962, '884, and '597 patents, for example. Or, thermal or laser energy is applied to desiccate the nucleus and to stiffen the annulus as described in the '149 patent, for example. Or, the nucleus and portions of the cephalad and caudal vertebral bodies are mechanically cut away to enlarge the disc space as described in the PCT '055 publication and in the '255 patent, for example. Irrigation fluid is introduced into the disc space or cavity and the fragments or desiccation by-products of the nucleus and any bone and annulus fragments are aspirated from the disc space or cavity. The irrigation and aspiration is effected through an access cannula positioned against the opening through the annulus of the herniated disc as disclosed in the '629 patent, for example, or through a lumen of the discectomy instrument, as disclosed in the '258 patent, for example. A measure of safety and accuracy is added to these operative procedures by the artiroscopic visualization of the annulus and other important structures which lie in the path of the instruments, such as the spinal nerve.

The above-described procedures involve invasive surgery that laterally exposes the anterior or posterior (or both) portions of the vertebrae and intervertebral spinal disc. Extensive muscular stripping and bone preparation can be necessary. As a result, the spinal column can be further weakened and/or result in surgery induced pain syndromes. Thus, presently used or proposed surgical fixation and fusion techniques involving the lower lumbar vertebrae suffer from numerous disadvantages.

Methods and apparatus for accessing the discs and vertebrae by lateral surgical approaches that purportedly reduce muscular stripping (and that are similar to those disclosed in the above-referenced '629 and '888 patents) are described in U.S. Pat. No. 5,976,146. The intervening muscle groups or other tissues are spread apart by a cavity forming and securing tool set disclosed in the '146 patent to enable endoscope aided, lateral access to damaged vertebrae and discs and to perform corrective surgical procedures. However, it is preferable to avoid the lateral exposure to correct less severe spondylolisthesis and other spinal injuries or defects affecting the lumbar and sacral vertebrae and discs.

A less intrusive posterior approach for treating spondylolisthesis is disclosed in U.S. Pat. No. 6,086,589, wherein a straight bore is formed through the sacrum from the exposed posterior sacral surface and in a slightly cephalad direction into the L5 vertebral body, preferably after realigning the vertebrae. A straight, hollow, threaded shaft with side wall holes restricted to the end portions thereof and bone growth material are inserted into the bore. A discectomy of the disc between L5 and S1 is preferably performed in an unexplained manner, and bone ingrowth material is also preferably inserted into the space between the cephalad and caudal vertebral bodies. Only a limited access to and alignment of S1 and L5 can be achieved by this approach because the distal ends of the straight bore and shaft approach and threaten to perforate the anterior surface of the L5 vertebral body. This approach is essentially a posteriolateral approach that is intended to fuse S1 and L5 and cannot access more cephalad vertebral bodies or intervertebral spinal discs.

In many of these procedures, a laterally extending space is prepared by removal of the disc to receive one or more disc implant, and insertion of a bone growth material, e.g. autologous bone, or a pre-formed, artificial, functional disc replacement implant. A number of disc shaped, functional disc replacement implants and methods of insertion have been proposed as disclosed, for example, in U.S. Pat. Nos. 5,258,031 and 6,019,792, for example. Other disc shaped or vertebral body replacement implants that are designed to encourage bone growth and effect fusion are shown in U.S. Pat. Nos. 5,514,180 and 5,888,223, for example. These devices and techniques are intended to overcome the disadvantages of purely surgical techniques to mechanically immobilize areas of the spine assisting in the eventual fusion of the treated adjacent vertebrae, and to maintain the length of the treated spinal motion segment to avoid shortening spinal cord and nerve segments. However, they require relatively large lateral exposure of the disc or vertebral body to excise the disc or vertebral body, shape the adjoining caudal and cephalad vertebral bodies and effect the implantation and fixation thereto. Thus, disadvantages to the present implants and surgical implantation techniques remain concerning the implantation procedures and involving post-surgical failure necessitating re-operation.

A further type of disc implant that has been clinically employed for spinal fusion comprises a hollow, cylindrical, titanium cage that is externally threaded and is screwed laterally into place in a lateral bore formed through the disc between two adjacent vertebrae. Typically, the lateral bore involves complete discectomy of the damaged disc and removal of portions of the cortical bone of the adjoining vertebral bodies to prepare a laterally and axially extending space to receive one or more disc implant. Bone grafts from cadavers or the pelvis or substances that promote bone growth are then packed into the hollow center of the cage to encourage bone growth (or ingrowth) through the cage pores to achieve fusion of the two adjacent vertebrae. Two such cage implants and the surgical tools employed to place them are disclosed in U.S. Pat. Nos. 5,505,732 and 5,700,291, for example. The cage implants and the associated surgical tools and approaches require precise drilling of a relatively large hole for each such cage laterally between two adjacent vertebral bodies and then threading a cage into each prepared hole. The exposed ends of the cage or side by side installed cages can irritate nerves causing pain to emerge again.

These approaches involve a virtually complete discectomy of the disc achieved by instruments introduced laterally through the patient's body to the disc site and manipulated to cut away or drill lateral holes through the disc and adjoining cortical bone. The large laterally drilled hole or holes can compromise the integrity of the vertebral bodies, and the spinal cord can be injured if they are drilled too posteriorly. The endplates of the vertebral bodies, which comprise very hard cortical bone and help to give the vertebral bodies needed strength, are usually weakened or destroyed during the drilling. The cylindrical cage or cages are now harder than the remaining bone of the vertebral bodies, and the vertebral bodies tend to collapse or "telescope" together. The telescoping causes the length of the vertebral column to shorten and can cause damage to the spinal cord and nerves that pass between the two adjacent vertebrae.

Therefore, it is often necessary to also mechanically stabilize the vertebrae on either side of the spinal disc that is augmented or removed so that fusion of the vertebral bodies can occur successfully without telescoping of the vertebral bodies or movement of the disc implants out of the prepared site. One technique for spinal fixation includes the immobilization of the spine by the use of spine rods of many different configurations that run generally parallel to the spine. Typically, the posterior surface of the spine is isolated and bone screws are first fastened to the pedicles of the appropriate vertebrae or to the sacrum and act as anchor points for the spine rods. The bone screws are generally placed two per vertebra, one at each pedicle on either side of the spinous process. Clamp assemblies join the spine rods to the screws. The spine rods are generally bent to achieve the desired curvature of the spinal column. Wires may also be employed to stabilize rods to vertebrae. These techniques are described further in U.S. Pat. No. 5,415,661, for example.

These types of rod systems can be effective, but require a posterior approach and implanting screws into or clamps to each vertebra over the area to be treated. To stabilize the implanted system sufficiently, one vertebra above and one vertebra below the area to be treated are often used for implanting pedicle screws. Since the pedicles of vertebrae above the second lumbar vertebra (L2) are very small, only small bone screws can be used which sometimes do not give the needed support to stabilize the spine. These rods and screws and clamps or wires are surgically fixed to the spine from a posterior approach, and the procedure is difficult. A large bending moment is applied to such rod assemblies, and because the rods are located outside the spinal column, they depend on the holding power of the associated components which can pull out of or away from the vertebral bone.

In a further approach disclosed in U.S. Pat. Nos. 4,553,273 and 4,636,217, both described in U.S. Pat. No. 5,735,899, two of three vertebrae are joined by surgically obtaining access to the interior of the upper and lower vertebral bodies through excision of the middle vertebral body. In the '899 patent, these approaches are referred to as "intraosseous" approaches, although they are more properly referred to as "interosseous" approaches by virtue of the removal of the middle vertebral body. The removal is necessary to enable a lateral insertion of the implant into the space it occupied so that the opposite ends of the implant can be driven upward and downward into the upper and lower vertebral bodies. These approaches are criticized as failing to provide adequate medial-lateral and rotational support in the '899 patent. In the '899 patent, an anterior approach is made, slots are created in the upper and lower vertebrae, and rod ends are fitted into the slots and attached to the remaining vertebral bodies of the upper and lower vertebrae by laterally extending screws. These approaches involve considerable damage to ligaments and tissue in the anterior access to the vertebral bones.

The use of radiopaque metal cages or other metal implants also makes it difficult to image the disc space with radiographic imaging equipment to assess the degree of fusion achieved by bone growth between the vertebral bodies separated by the cages. Laterally insertable, rigid carbon fiber and more flexible polymeric disc implants are under study as replacements for metal implants.

Alternatively, the use of a deflated porous fabric bag that is laterally inserted into a prepared cavity and inflated with bone growth encouraging material is disclosed in U.S. Pat. No. 5,549,679. The prepared cavity is substantially ovaloid and includes the removed disc and a portion of the adjoining vertebral bodies. The filling of the bag under pressure tends to distract, i.e., to separate, the adjoining vertebral bodies to the physiologic separation that would be provided by the undamaged disc. The porous bag opening is closed in a number of ways to retain the material it is filled with. This porous bag is distinguished from several other artificial disc designs described in the '679 patent, including an artificial disc with an elastomeric core (U.S. Pat. No. 5,071,437) or filled with hydrogel beads (U.S. Pat. No. 5,192,326).

In a further disc augmentation approach described in U.S. Pat. No. 5,888,220, the disc is accessed laterally through the patient's body, the annulus is perforated unless it is already rent, and a partial discectomy is performed to remove most or all of the nucleus to create a space within the annulus. Then, a mass of curable biomaterials is injected into the prepared space and the material is cured in situ. In one variation, a deflated balloon is inserted into the prepared space, and the mass of curable biomaterials is injected into the prepared space and the material is cured in situ, leaving the filled balloon and solidified biomaterial in place.

A compilation of many of the above described surgical techniques and spinal implants and others that have been used clinically is set forth in certain chapters of the book entitled *Lumbosacral and Spinopelvic Fixation*, edited by Joseph Y. Margolies et al. (Lippincott-Raven Publishers, Philadelphia, 1996). Attention is directed particularly to Chapters 1, 2, 17, 18, 38, 42 and 44.

In "Lumbopelvic Fusion" (Chapter 38, by Prof. Rene P. Louis, Md.) techniques for repairing a spondylolisthesis, in this case, a severe displacement of L5 with respect to S1 and the intervening disc, are described and depicted. An anterior lateral exposure of L5 and S1 is made, a discectomy is performed, and the orientation of L5 to S1 is mechanically corrected using a reduction tool, if the displacement is severe. A fibula graft or metal Judet screw is inserted as a dowel through a bore formed extending caudally through L5 and into S1. When the screw is used, bone growth material, e.g., bone harvested from the patient, is inserted into the bore alongside the screw, and the disc space is filled with bone sutured to the screw to keep it in place between the vertebral surfaces to act as a spacer implant occupying the extracted disc between L5 and S1. External bridge plates or rods are also optionally installed. The posterolateral or anterior lateral approach is necessitated to correct the severe spondylolisthesis displacement using the reduction tool and results in tissue injury. Because of this approach and need, the caudal bore and inserted the Judet screw can only traverse L5 and S1.

A similar anterior approach for treating spondylolisthesis is disclosed in U.S. Pat. No. 6,056,749. In this approach, a bore hole is formed in a cephalad vertebral body and extends through the intervening disc into a caudal vertebral body, the disc is removed, a disc cage is inserted laterally into the disc space, and an elongated, hollow threaded shaft is inserted into the bore and through a hole in the disc cage. The disc cage takes the place of the harvested bone disc inserts and its interlocking intersection with the shaft takes the place of the sutures employed to tie the harvested bone disc inserts to the screw in the technique described in the above-referenced Chapter 38 publication.

Turning to a further spinal disorder, the vertebral bodies can thin and weaken with the development and progression of osteoporosis and certain eating disorders to the point that one or more vertebral body compression fractures occur as described in U.S. Pat. Nos. 4,969,888, 5,972,015 and 6,066, 154. Vertebral compression fractures of healthy vertebral bodies can also occur due to injury. In severe cases, the vertebral body tends to collapse, shortening the vertebral body and the spine and inducing an aberrant localized spinal curvature. As noted in the '888 patent, osteoporotic vertebral body compression fractures are currently treated with bed rest, analgesics, and intravenous hydration during the first week after onset of the problem. These steps are followed by the prescription of a soft or firm spinal corset, depending upon the physician's preference. In most cases, the corset is not worn because the patient suffers much discomfort and oftentimes greater discomfort than that due to the fracture of the vertebral body. The fracture pain lasts from two to eight months. In many cases, patients with osteoporotic vertebral body collapse fractures require about one week in an acute care hospital and two to three weeks in an extended care facility until they are able to move about independently and with only moderate pain. Current treatment does not substantially alter the conditions of the vertebral body.

The '888 patent describes a "balloon-assisted vertebroplasty" method of restoring the vertical height of a collapsed, compression fractured vertebral bone through a posterolateral approach from an entry point on the skin determined radiologically and is located approximately 10 cm from the midline and just inferior to a rib if present at that level. A guide pin is extended from the incision to the vertebral body and through the cortical bone and a predetermined distance into the cancellous bone. A cannula is inserted over the guide pin and its distal end is attached to the exterior cortical bone of the vertebral body. A drill is extended through the cannula and used to drill a hole into the cancellous bone to enlarge the cavity to be treated. A deflated, expandable balloon is inserted through the cannula and inflated inside the vertebral body into a disc or checker shape. The expansion of the balloon compacts the cancellous bone against the inner surface of the outer cortical wall of the vertebral body thereby further enlarging the cavity and, it is asserted, filling the fractures in the cortical bone. The balloon expansion may also restore the height of the vertebral body to some extent. The balloon is then deflated and removed, and the cavity is irrigated with saline. The cavity is simultaneously aspirated and filled with a flowable synthetic bone material or methyl methacrylate cement that is allowed to set to a hardened condition through the cannula. It is asserted that the compacted cortical bone or bone marrow will substantially prevent flow through the fracture.

The '015 and '154 patents disclose generally the same procedure steps but employ improved, irregularly shaped, balloons that approximate the inner shape of the vertebral bodies they are inflated within in order to maximally compress cancellous bone. The balloons are made of inelastic material and are kept in their defined configurations when inflated by various shape restraints. This procedure is also referred to as a "Kyphoplasty", by Kyphon, Inc., the assignee of the '015 and '154 patents.

There are other therapeutic treatments for encouraging bone growth within a vertebral body or to fuse vertebral bodies together with or without a pre-formed spinal disc replacement implant that involve injection of bone growth materials into the disc or vertebral body or the application of electrical energy to stimulate bone growth. Several natural or artificial osteoconductive, osteoinductive, osteogenic or other fusion enhancing materials are disclosed in U.S. Pat. No. 6,123,705. A system and method for delivering electrical energy to a pre-formed spinal disc replacement implant to promote bone growth and fusion about the implant and between the opposed endplates of the cephalad and caudal vertebral bodies are disclosed in U.S. Pat. No. 6,120,502.

A wide variety of orthopedic implants have also been proposed or clinically employed to stabilize broken bones or secure artificial hip, knee and finger joints. Frequently, rods or joint supports are placed longitudinally within longitudinal bores made in elongated bones, e.g., the femur. A surgical method is disclosed in U.S. Pat. No. 5,514,137 for stabilizing a broken femur or other long bones using an elongated rod and resorbable cement. To accomplish a placement of a rod into any single bone, an end of a bone is exposed and a channel is drilled from the exposed end to the other end. Thereafter, a hollow rod is inserted, and resorbable cement is injected through the hollow rod, so as to provide fixation between the distal end of the rod and the cancellous tissue that surrounds the rod. A cement introducer device can also be used for the injection of cement. A brief reference is made in the '137 patent to the possibility of placing rods in or adjacent to the spine in the same manner, but no particular approach or devices are described.

Drilling tools are employed in many of the above described surgical procedures to bore straight holes into the vertebral bones. The boring of curved bores in other bones is described in U.S. Pat. Nos. 4,265,231, 4,541,423, and 5,002,546, for example. The '231 patent describes an elongated drill drive shaft enclosed within a pre-curved outer sheath that is employed to drill curved suture holding open ended bores into bones so that the suture passes through both open ends of the bore. The '423 patent describes an elongated flexible drill drive shaft enclosed within a malleable outer sheath that can be manually shaped into a curve before the bore is formed. The '546 patent describes a complex curve drilling tool employing a pivotal rocker arm and curved guide for a drill bit for drilling a fixed curve path through bone. All of these approaches dictate that the curved bore that is formed follow the predetermined and fixed curvature of the outer sheath or guide. The sheath or guide is advanced through the bore as the bore is made, making it not possible for the user to adjust the curvature of the bore to track physiologic features of the bone that it traverses.

All of the above-described patents and other patents referenced herein that access a single spinal disc or vertebra to perform the above-described therapies, do so from a lateral approach that involves weakening of the spinal fusion segment. There remains a need for methods and apparatus for performing therapeutic procedures in the spine in a minimally invasive, low trauma, manner.

SUMMARY OF THE INVENTION

There is provided in accordance with one aspect of the present invention, a method of augmenting the spine. The method comprises the steps of providing an elongate augmentation catheter, having a proximal end, a distal end, and at least one lumen extending therethrough. The distal end is advanced through at least one vertebral body and into at least one disc. An augmentation media is expressed from the catheter to augment the spine. Alternatively, at least a first media is expressed from the catheter into at least one of the disc and the vertebral body. In certain procedures, at least a second media is expressed from the catheter into the other of the disc or the vertebral body.

In one embodiment, the expressing step comprises expressing the first media from a first lumen in the catheter. The second media may be expressed from a second lumen in the catheter, or sequentially from the first lumen. The advancing step may comprise advancing the distal end through at least two or three or four or more vertebral body end plates. The first media may comprise a nucleus augmentation material, and the second media may comprise a bone growth facilitator.

In one exemplary procedure, an access catheter is introduced through a paracoccygeal access point and advanced toward the anterior surface of the sacrum. The access catheter is swept along the concave surface of the sacrum, displacing the bowel, until the distal end resides at an access point on the spine. A drilling device is introduced into the spine at the access point, and advanced through at least one vertebral body end plate to create a lumen or bore. Media is introduced from an augmentation catheter into the spine.

The method may additionally comprise the steps of either detaching at least a portion of the catheter and leaving that portion within the spine, or proximally retracting the catheter from the spine.

In accordance with another aspect of the present invention, there is provided a method of treating the spine. The method comprises the steps of identifying an access site on the spine, and advancing a device through the access site and into the spine. The device is further advanced axially through at least two vertebral body end plates in the spine, and into a treatment zone. A bone growth material is expressed from the device within the treatment zone. At least a portion of the device may also be deployed within the treatment zone.

In one application of the invention, the access site in on the sacrum. In another aspect, the access site is on the thoracic spine. The device may be percutaneously introduced through the skin prior to the advancing step. The advancing step may comprise advancing the device along a linear path through the spine, or along a nonlinear path through the spine.

There is provided in accordance with another aspect of the present invention, a spinal augmentation catheter. The catheter comprises an elongate tubular body, having a proximal end and a distal end. A first lumen extends through the body, and a second lumen extends through the body. A first port is provided on the body in communication with the first lumen, and a second port is provided on the body in communication with the second lumen. The first and second ports are spaced axially apart along the body such that the first port may be positioned within a first vertebral body while the second port is positioned within a first disc space for infusion of a first media into the first vertebral body and a second media into the first disc space.

In one embodiment, the spinal augmentation catheter is further provided with a detachable joint, for detaching at least a portion of the tubular body within the spine. In another application, the tubular body is provided with at least one flex point for permitting flexing of the catheter. A further embodiment includes at least a third port in communication with the first lumen, and spaced axially apart from the first port such that the third port may be positioned within a second vertebral body while the first port is positioned within the first vertebral body.

In accordance with another aspect of the present invention, there is provided a method of treating the spine. The method comprises the steps of identifying a site on the surface of the sacrum, and forming a lumen from the site through the sacrum, through a disc and axially into at least one vertebrae. The interior of the spine is directly observed by introducing an endoscope into the lumen, and a procedure is thereafter performed using the lumen. The procedure may be a diagnostic or therapeutic procedure. The lumen may extend at least as far as the L4 vertebrae. The lumen may be either linear or curved.

In accordance with a further aspect of the present invention, there is provided a method of treating the spine. The method comprises the steps of identifying a site on the anterior surface of the sacrum. A lumen is formed from the site through the sacrum, through a disc and into at least one vertebrae. A tubular fusion device is axially positioned within the lumen. The fusion device may have an external thread. The fusion device may additionally include a side wall having a plurality of apertures therethrough. The lumen may extend at least as far as the L4 vertebrae. The method may additionally comprise the step of introducing a bone growth material into the lumen.

In accordance with another aspect of the present invention, there is provided a method of fusing the spine. The method comprises the steps of identifying a site on the sacrum. A lumen is formed from the site through the sacrum through a disc and into at least one vertebrae. A fusion implant is introduced axially through the lumen, the implant comprising at least one radially outwardly extending bone engagement structure.

In one embodiment, the bone engagement structure comprises a helical thread. The introducing step may further comprise introducing a bone growth material into the lumen.

Further features and advantages of the present invention will become apparent to those of ordinary skill in the art in view of the detailed description of preferred embodiments which follows, when considered together with the attached drawings and claims.

BRIEF DESCRIPTION OF THE DRAWINGS

FIGS. 1-3 are lateral, posterior and anterior views of the lumbar and sacral portion of the spinal column depicting the visualized PAIFL and AAIFL extending cephalad and axially from the posterior laminectomy site and the anterior target point, respectively;

FIG. 4 is a sagittal caudal view of a lumbar vertebrae depicting a TASIF axial spinal implant or rod within a TASIF axial bore formed following the visualized PAIFL or AAIFL of FIGS. 1-3;

FIG. 5 is a sagittal caudal view of a lumbar vertebrae depicting a plurality, e.g., 2, TASIF axial spinal implants or rods within a like plurality of TASIF axial bores formed in parallel with the visualized PAIFL or AAIFL of FIGS. 1-3;

FIG. 15 is a schematic side elevational view of a dual lumen augmentation media infusion catheter in accordance with one aspect of the present invention.

FIG. 16 is a cross sectional view taken along the line 16-16 of FIG. 15.

FIG. 17 is a cross sectional view taken along the line 17-17 of FIG. 15.

DETAILED DESCRIPTION OF THE PREFERRED EMBODIMENT

Figure 6:
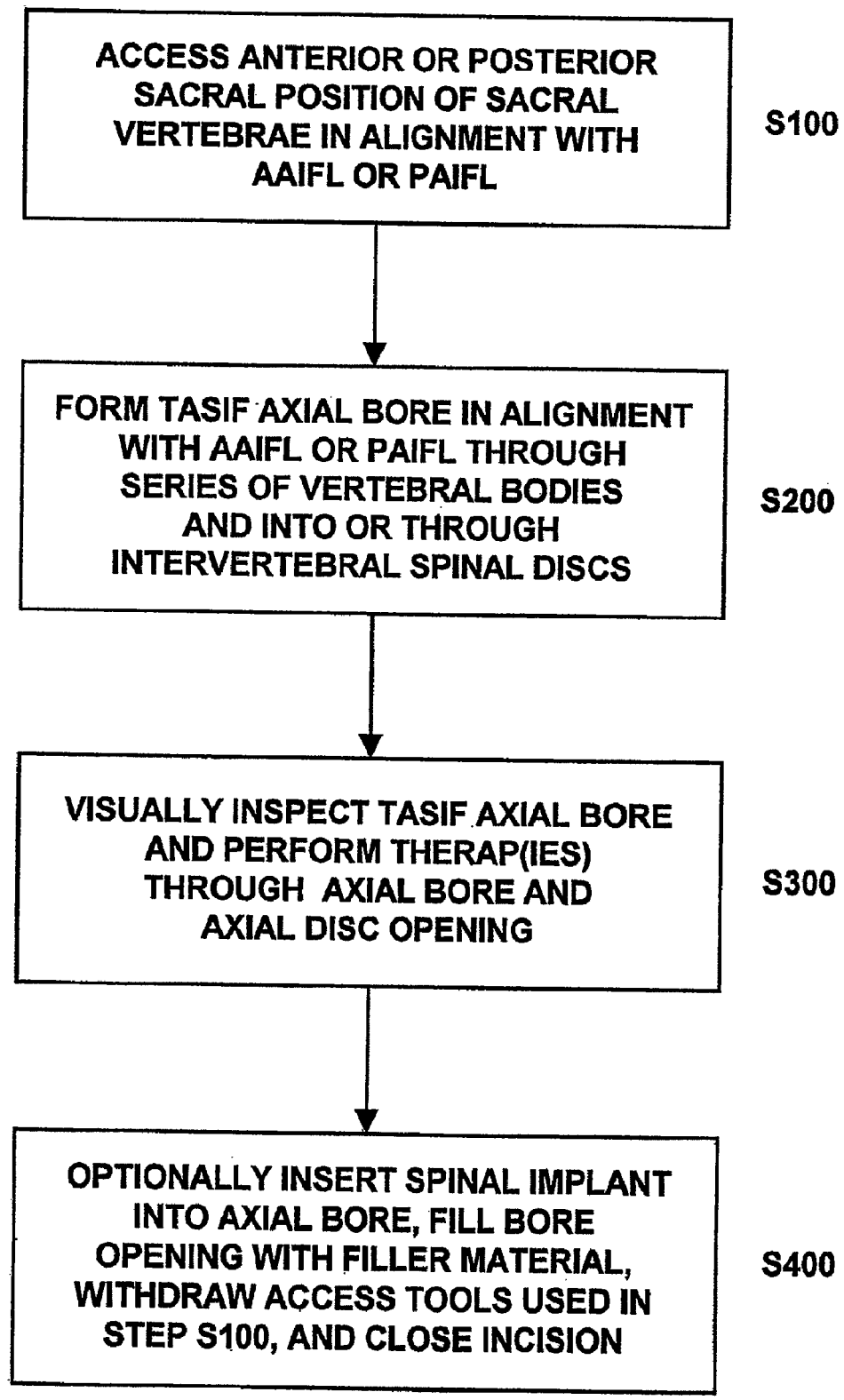
FIG. 6 is a simplified flow chart showing the principal surgical preparation steps of percutaneously accessing a posterior or anterior target point of the sacrum and forming a percutaneous tract following the visualized PAIFL or AAIFL of FIGS. 1-3, as well as subsequent steps of forming the TASIF bore(s) for treatment of accessed vertebral bodies and intervening discs and of implanting axial spinal implants therein.

The methods and surgical instrumentation and axial spinal implants disclosed in co-pending, commonly assigned, related patent applications U.S. patent application Ser. No. 09/640,222 filed Aug. 16, 2000, U.S. patent application Ser. No. 09/684,820 filed Oct. 10, 2000, U.S. patent application Ser. No. 09/710,369 filed Nov. 10, 2000, U.S. patent application Ser. No. 09/709,105 filed Nov. 10, 2000, U.S. patent application Ser. No. 09/782,583 filed Feb. 13, 2001, U.S. patent application Ser. No. 09/848,556 filed May 3, 2001, U.S. patent application Ser. No. 09/782,534 filed Feb. 13, 2001 can be employed in the practice of the present invention, and the disclosures of the above-identified applications are hereby incorporated in their entireties herein by reference.

FIGS. 1-3 schematically illustrate the anterior and posterior TASIF surgical approaches in relation to the lumbar region of the spinal column, and FIGS. 4-5 illustrate the location of the TASIF implant or pair of TASIF implants within a corresponding posterior TASIF axial bore 22 or anterior TASIF axial bore 152 or pair of TASIF axial bores 221, 222 or 1521, 1522. Two TASIF axial bores and axial spinal implants or rods are shown in FIG. 5 to illustrate that a plurality, that is two or three or more, of the same may be formed and/or employed in side by side relation in parallel alignment with the AAIFL or PAIFL or diverging from the AAIFL or PAIFL in the cephalad direction. Preferred TASIF surgical approaches for providing anterior and posterior trans-sacral access depicted in FIGS. 1-3 and preparing the TASIF axial bores 22 or 152 or 221, 222, or 1521, 1522 shown in FIGS. 4 and 5 are illustrated in the above-referenced '105 and '748 applications.

The lower regions of the spinal column comprising the coccyx, fused sacral vertebrae S1-S5 forming the sacrum, and the lumbar vertebrae L1-L5 described above are depicted in a lateral view in FIG. 1. The series of adjacent vertebrae located within the human lumbar and sacral spine have an anterior aspect, a posterior aspect and an axial aspect, and the lumbar vertebrae are separated by intact or damaged intervertebral spinal discs labeled D1-D5 in FIG. 1. FIGS. 2 and 3 depict the posterior and anterior views of the sacrum and coccyx.

The method and apparatus for forming an anterior or posterior TASIF axial bore initially involves accessing an anterior sacral position, e.g. an anterior target point at the junction of S1 and S2 depicted in FIGS. 1 and 3, or a posterior sacral position, e.g. a posterior laminectomy site of S2 depicted in FIGS. 1 and 2. One (or more) visualized, imaginary, axial instrumentation/fusion line extends cephalad and axially in the axial aspect through the series of adjacent vertebral bodies, L4 and L5 in this illustrated example. The visualized AAIFL through L4, D4, L5 and D5 extends relatively straight from the anterior target point along S1 depicted in FIGS. 1 and 3, but may be curved as to follow the curvature of the spinal column in the cephalad direction. The visualized PAIFL extends in the cephalad direction with more pronounced curvature from the posterior laminectomy site of S2 depicted in FIGS. 1 and 2. A preoperative CT scan or magnetic resonance imaging (MRI) study of the patient's spine is conducted to visualize and map the AAIFL or PAIFL.

FIG. 6 depicts, in general terms, the surgical steps of accessing the anterior or posterior sacral positions illustrated in FIGS. 1-3 (S100) forming posterior and anterior TASIF axial bores (S200), optionally inspecting the discs and vertebral bodies, performing discectomy or discoscopy, disc augmentation, and vertebral bone reinforcement, balloon-assisted vertebroplasty or vertebroplasty (S300), and implanting posterior and anterior axial spinal implants and rods or plugs into the axial bore(s) (S400) in a simplified manner. In step S100, access to the anterior or posterior sacral position, that is the anterior target point of FIG. 3 or the posterior laminectomy site of FIG. 2 is obtained, and the anterior or posterior sacral position is penetrated to provide a starting point for each axial bore that is to be created. Then, one or more axial bore is bored from each point of penetration extending in alignment with either the PAIFL or AAIFL cephalad and axially through the vertebral bodies of the series of adjacent vertebrae and any intervertebral spinal discs (S200). The axial bore(s) can traverse one or more vertebral body cephalad to the sacral vertebral bodies S1, S2 and any intervertebral disc and can terminate at a cephalad end within a particular vertebral body or spinal disc. The axial bore may be visually inspected using an endoscope to determine if the procedures of step S300 should be performed.

The performance of step S100 in the anterior and/or posterior TASIF procedures may involve drilling a pilot hole, smaller in diameter than the TASIF axial bore, in the prescribed alignment with the AAIFL and/or PAIFL in order to complete the formation of the anterior and/or posterior percutaneous tracts. Certain of the therapeutic procedures of steps S300 and S400 may optionally be completed through the AAIFL/PAIFL pilot hole following step S100, rather than following the enlargement of the pilot hole to form the TASIF axial bore in step S200.

Step S100 preferably involves creation of an anterior or posterior percutaneous pathway that enables introduction of further tools and instruments for forming an anterior or posterior percutaneous tract extending from the skin incision to the respective anterior or posterior target point of the sacral surface or, in some embodiments, the cephalad end of a pilot hole over which or through which further instruments are introduced as described in the above-referenced '222 application. An "anterior, presacral, percutaneous tract" 26 (FIG. 1) extends through the "presacral space" anterior to the sacrum. The posterior percutaneous tract or the anterior, presacral, percutaneous tract is preferably used to bore one or more respective posterior or anterior TASIF bore in the cephalad direction through one or more lumbar vertebral bodies and intervening discs, if present. "Percutaneous" in this context simply means through the skin and to the posterior or anterior target point, as in transcutaneous or transdermal, without implying any particular procedure from other medical arts. However, the opening in the skin is preferably minimized so that it is less than 4 cm across, preferably less than 2 cm, and, in certain applications, less than 1 cm across. The percutaneous pathway is generally axially aligned with the AAIFL or the PAIFL extending from the respective anterior or posterior target point through at least one sacral vertebral body and one or more lumbar vertebral body in the cephalad direction as visualized by radiographic or fluoroscopic equipment.

It should be noted that the formation of the anterior tract 26 shown in FIG. 1 through presacral space under visualization described above is clinically feasible as evidenced by clinical techniques described by J. J. Trambert, Md., in "Percutaneous Interventions in the Presacral Space: CT-guided Precoccygeal Approach—Early Experience (Radiology 1999; 213: 901-904).

Certain of the therapeutic procedures of the present invention are conducted through relatively straight or curved anterior TASIF bores or curved posterior TASIF bores or pilot holes. Introduction of axial spinal implants and instruments for performing discoscopy to inspect the accessed discs, discectomies and/or disc augmentation/replacement and/or vertebroplasty, balloon-assisted vertebroplasty, fusion, alignment, drug delivery, electrical stimulation, or other therapies, is enabled by the provision of the percutaneous pathway and formation of the anterior or posterior TASIF bore(s).

The bore forming tool sets comprise elongated drill shaft assemblies supporting distal boring tools, e.g., mechanical rotating drill bits, burrs, augurs, abraders, or the like (collectively referred to as boring heads or drill bits for convenience), that can be manipulated in use to bore a straight or curved axial bore. Suitable bore forming tools are disclosed in the above-referenced United States Patent Applications. However, the TASIF axial bores can be formed by other tools that mechanically puncture or penetrate vertebral bodies and intervertebral discs or otherwise form TASIF axial bores in any diameter or cross-section and that follow any alignment with the axis of the spine as visualized by the AAIFL or PAIFL. For convenience, the posterior and anterior TASIF axial bores are referred to as being formed or bored herein.

Figure 7:
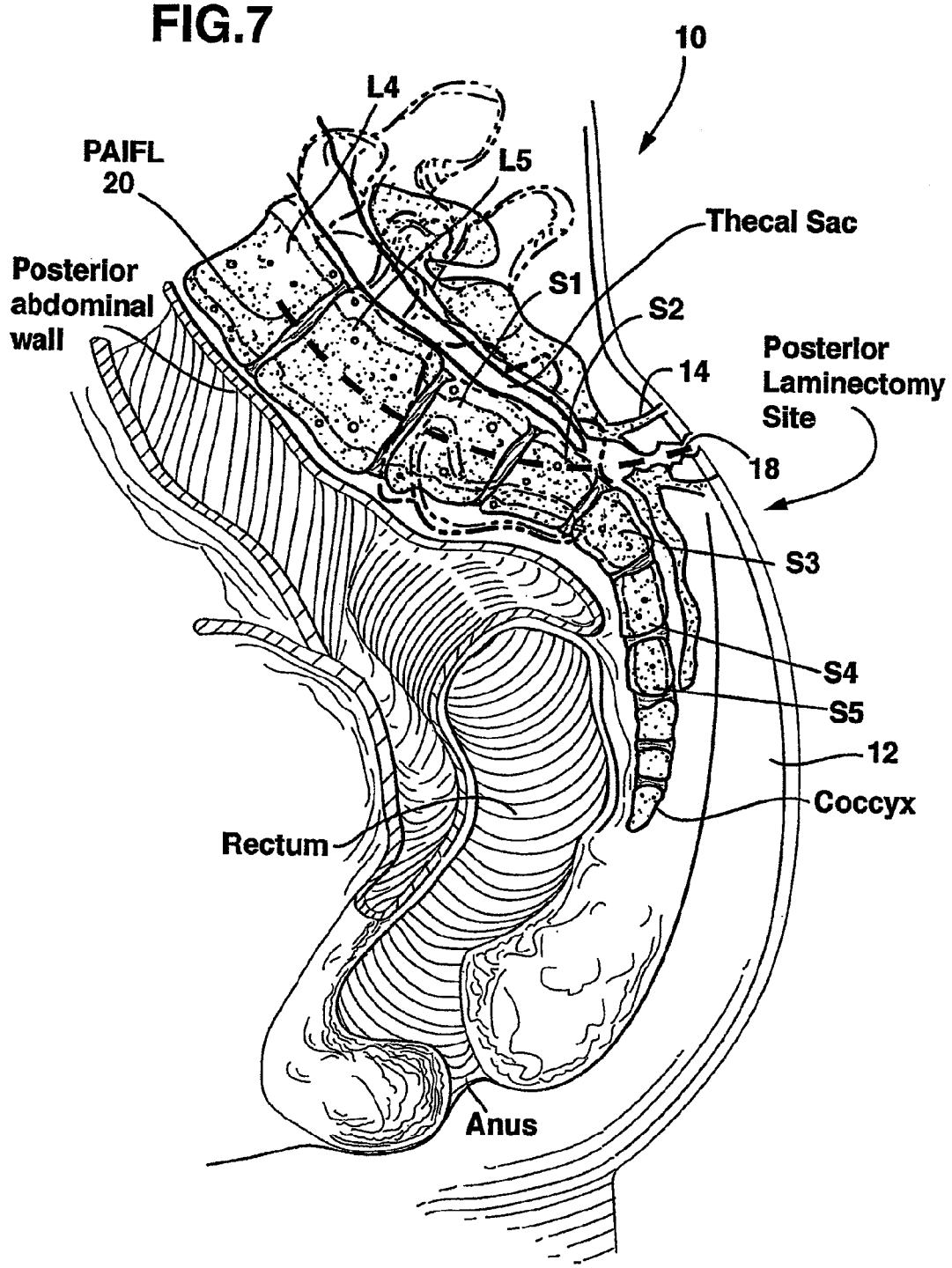
FIG. 7 illustrates, in a partial cross-section side view, one manner of obtaining access to a posterior target point for forming a posterior TASIF axial bore through sacral and lumbar vertebrae and intervening discs axially aligned with the visualized PAIFL of FIGS. 1 and 2.
Figure 8:
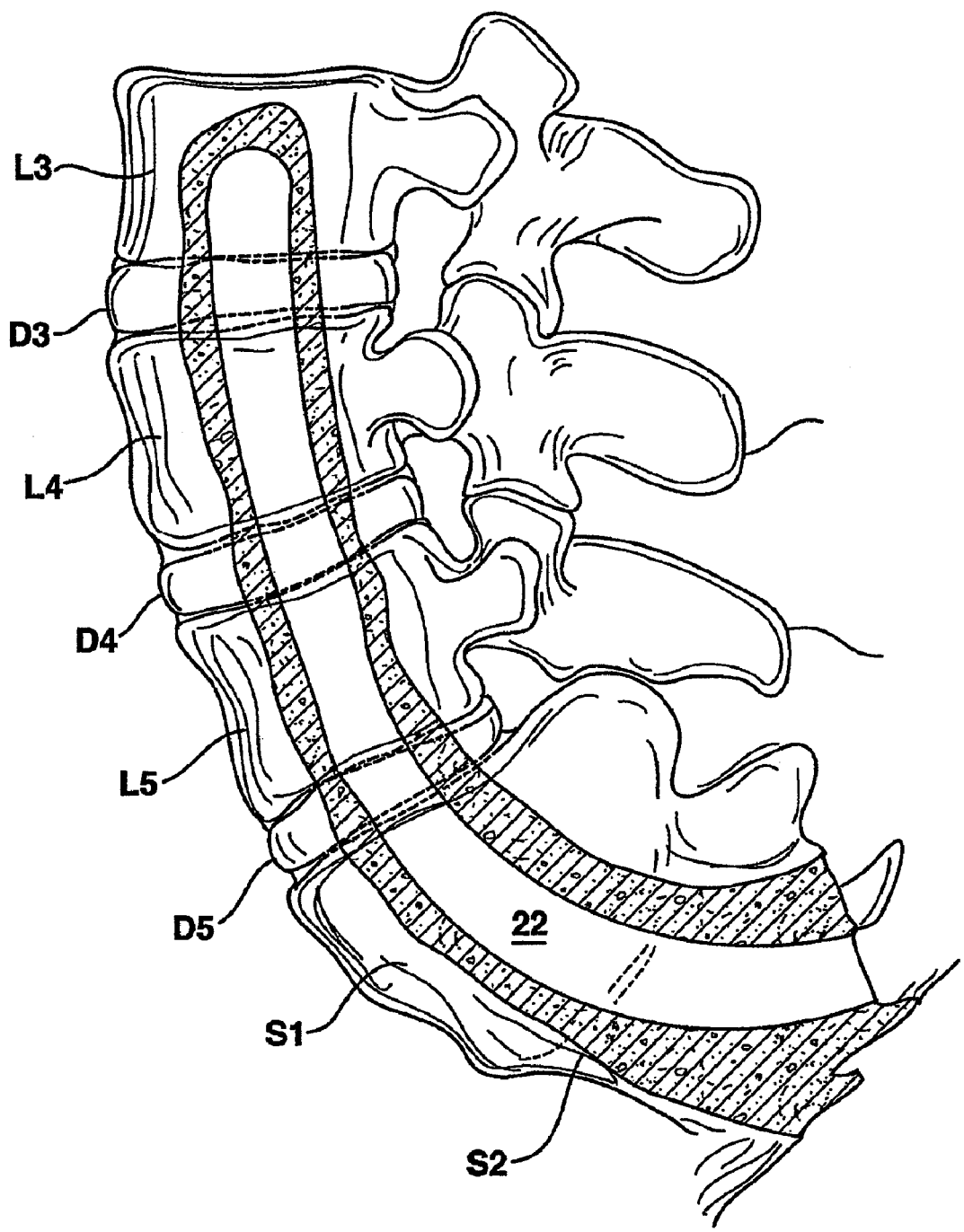
FIG. 8 is an enlarged partial cross section view illustrating a posterior TASIF axial bore through sacral and lumbar vertebrae and intervening discs axially aligned with the visualized PAIFL of FIGS. 1 and 2.

FIGS. 7 and 8 illustrate step S100 for forming the posterior percutaneous tract and the posterior TASIF axial bore 22 formed in step S200 and extending through sacral and lumbar vertebrae and intervening discs axially aligned with the visualized PAIFL of FIGS. 1 and 2 using a boring tool of the type described in more detail in the above-referenced '105 application. The same steps can be employed to form a pilot hole of step S100 that can be enlarged in step S200. In this case, a small diameter bore forming tool (e.g. 3.0 mm diameter) is used to first bore a small diameter curved pilot hole following the imaginary, visualized PAIFL 20, such as through S1, L5 and L4 in step S100. Then, the boring tool is removed, and a guidewire having a threaded distal screw-in tip is advanced through the pilot hole and screwed into to the caudal end of the pilot hole and into cephalad portion of the L4 body. An over-the-wire bore enlarging tool having a flexible body capable of tracking the curved guidewire is fitted over the proximal end of the guidewire and manually or mechanically rotated and advanced along it in step S200. In this way, the small pilot hole diameter is enlarged to form the anterior TASIF axial bore 22 having a diameter e.g. a 10.0 mm diameter, and the enlarging tool is then removed.

It will be understood that the illustrated diameter of the posterior TASIF axial bore hole 22 relative to sizes of the vertebral bodies is merely exemplary, and that it is contemplated that the pilot hole and bore hole diameters can range from about 1-10 mm and 3-30 mm, respectively. Moreover, it will be understood that a plurality of such posterior TASIF axial bores 221 . . . 22n can be formed in side by side or diverging relation generally aligned with the PAIFL. Although more can be used and remain within the scope of the present invention, one or two or three or four side by side (parallel or diverging) axial bores are presently contemplated.

In FIG. 7, the posterior surface of the sacrum is exposed in step S100 as described in the above-referenced applications. The area of the patient's skin surrounding the incision site is surgically prepped, and the anus is excluded from the surgical field using adhesive drapes. The actual dermal entry site may be determined by the prone, preoperative CT scan or magnetic resonance imaging (MRI) study that maps the PAIFL. In step S100, an incision is made in the patient's skin over the posterior sacral surface of S2, and the subcutaneous tissue is separated to expose the posteriorly extending, bony ridge of the posterior sacral surface. A small laminectomy 14 is performed through the posterior ridge of the sacrum inferior. The thecal sac and nerve roots that are exposed by the laminectomy are gently retracted, and the terminal portion of the spinal canal is exposed.

An elongated drill shaft assembly (not shown) is axially aligned with the PAIFL at the posterior target point so that the initial penetration of the sacrum is substantially at right angles to the exposed sacral surface. A drill guide for receiving the drill drive shaft assembly for drilling or boring a posterior TASIF axial bore 22 from S2 along the visualized PAIFL may optionally be attached to S2 and extended posteriorly through the exposed spinal canal and skin incision.

The progress of the drill bit is observed using conventional imaging equipment. As the elongated drill shaft assembly is extended anteriorly in the cephalad direction, a curvature is introduced in the cephalad segment of the posterior TASIF axial bore 22 as shown in FIG. 8. It is necessary to maintain the plane of curvature of the distal segment aligned to the curvature of the spine. In this way, the drill bit advances through the sacral vertebrae in the cephalad direction and toward the lumbar vertebral bodies while staying within the spongy, cancellous bone of each vertebral body. Theoretically, any number of vertebral bodies of the spine can be bored through in the cephalad axial direction. The cephalad end of the posterior TASIF axial bore 22 can terminate within a vertebral body or within a disc or disc space.

Figure 9:
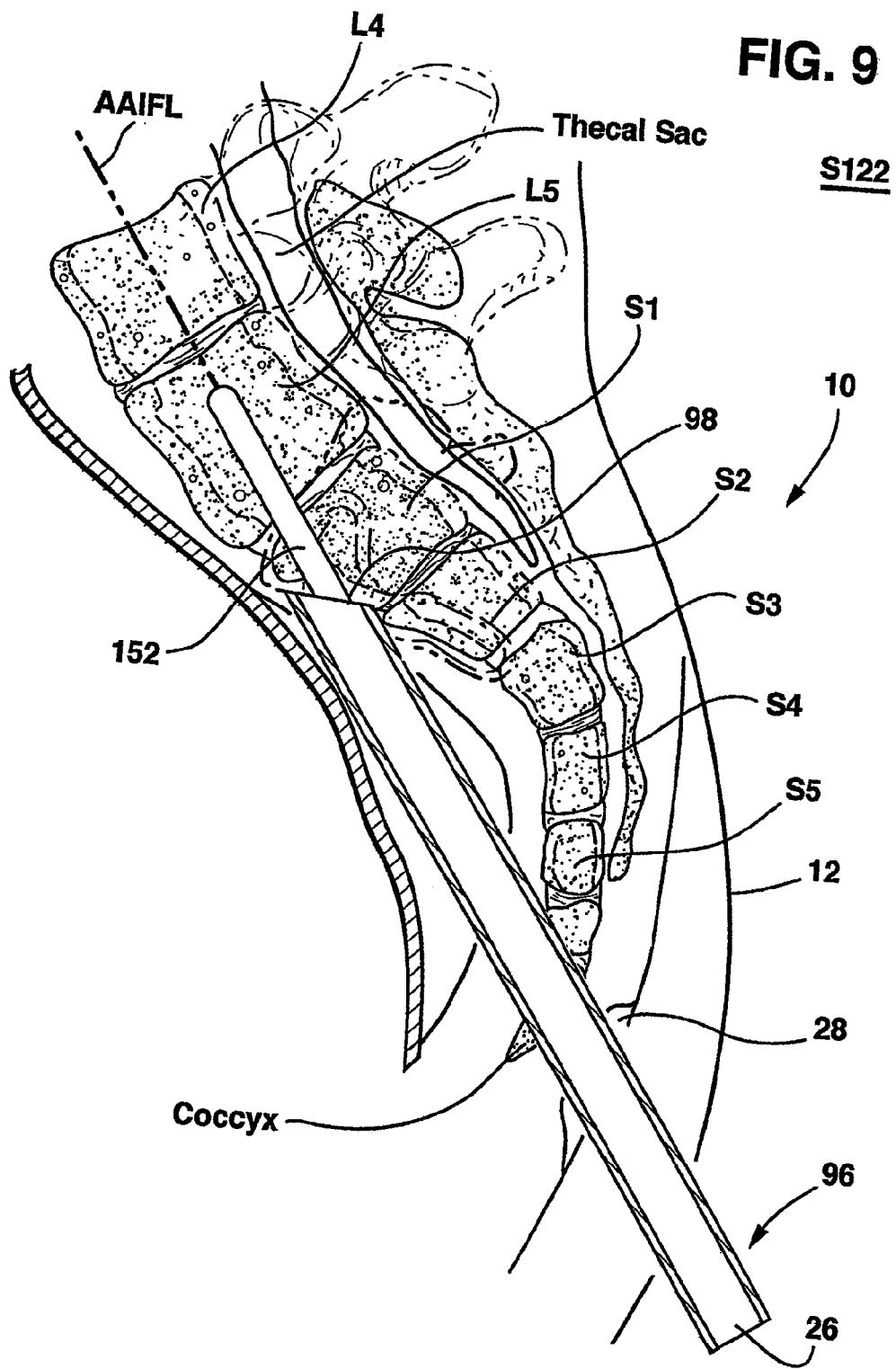
FIG. 9 illustrates, in a partial cross-section side view, one manner of obtaining access to an anterior target point for forming an anterior TASIF axial bore through sacral and lumbar vertebrae and intervening discs axially aligned with the visualized AAIFL of FIGS. 1 and 2.
Figure 10:
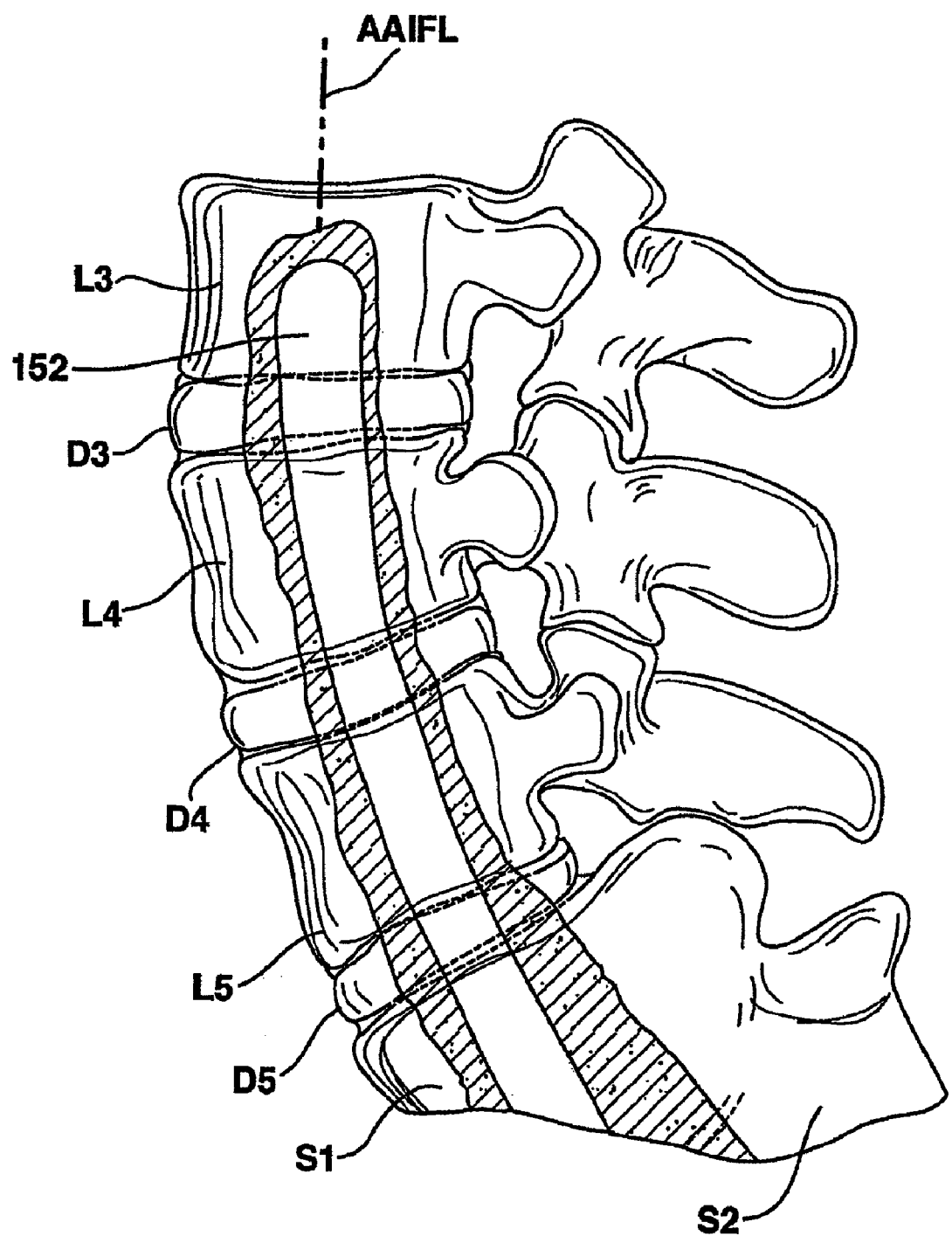
FIG. 10 is an enlarged partial cross-section view illustrating an anterior TASIF axial bore through sacral and lumbar vertebrae and intervening discs axially aligned with the visualized AAIFL of FIGS. 1 and 2.

FIGS. 9 and 10 illustrate the anterior percutaneous tract formed in step S100 and the anterior TASIF axial bore 22 formed in step S200 and extending through sacral and lumbar vertebrae and intervening discs axially aligned with the visualized AAIFL of FIGS. 1 and 2 using a boring tool of the type described in more detail in the above-referenced applications. The same steps can be employed to form a pilot hole of step S100 that can be enlarged in step S200 as described above. It will be understood that the illustrated diameter of the anterior TASIF axial bore hole 152 relative to sizes of the vertebral bodies is merely exemplary, and that it is contemplated that the pilot holes and bore hole diameters can range from about 1-10 mm and 3-30 mm, respectively. Moreover, it will be understood that a plurality of such anterior TASIF axial bores 1521 . . . 152n can be formed in side by side or diverging relation generally aligned with the AAIFL.

The anterior TASIF axial bore(s) can be relatively straight from the anterior target point into or through at least the caudal lumbar vertebrae and intervertebral discs. But, it may be desirable or necessary to form a curved anterior TASIF axial bore(s) particularly as the bore(s) is extended in the cephalad direction to maintain the plane of curvature of the cephalad segment of the TASIF axial bore(s) aligned to the curvature of the spine. In this way, the drill bit advances through the sacral vertebrae in the cephalad direction while staying within the spongy, cancellous bone of each vertebral body. Theoretically, any number of vertebral bodies of the spine can be bored through in the cephalad direction. The cephalad end of the posterior TASIF axial bore(s) 152 can terminate within a vertebral body or within a disc or disc space.

In accordance with the present invention, a variety of therapeutic procedures can be performed in step S300 or step S400 after the curved posterior or curved or straight anterior TASIF axial bore(s) is formed employing instruments, axial spinal implants, spinal disc implants and materials. Certain of the therapies or therapeutic procedures can be completed in step S300 without an axial spinal implant also being implanted in step S400. Step S400 may also be performed in certain cases without a therapeutic procedure being performed in step S300. The therapeutic procedures that are performed using such instruments, axial spinal implants, spinal disc implants and materials of the present invention include, but are not limited to one or more of: (1) performing a discoscopy by inserting an endoscope and inspecting the condition of the vertebral bodies and spinal discs; (2) performing a simple fusion by inserting bone growth materials into the TASIF axial bore(s) in step S400; (3) performing a partial discectomy or complete discectomy of a disc accessed through a TASIF axial bore in step S300; (4) performing a vertebroplasty or balloon-assisted vertebroplasty to a fractured vertebral body accessed through a TASIF axial bore in step S300; (5) inserting an artificial disc implant or autologous/homologous bone or bone growth material into the disc space following a complete discectomy of a disc accessed through a TASIF axial bore in step S400 to encourage fusion or to function as a functional disc replacement; (6) following a partial discectomy removing at least a portion of the nucleus, inserting an inflatable envelope or other disc implant or a material into the disc space to augment a disc accessed through a TASIF axial bore in step S300 to encourage fusion or to function as a functional disc replacement; (7) inserting axial spinal implants into the bore(s) as a single therapy or in conjunction with any of the preceding listed therapies (1)-(6) in step S400; (8) inserting axial spinal implants providing distraction of two or more vertebrae across one or more intervertebral disc and/or shock absorption due to loads applied axially to the spine in step S400; (9) extending an electrical lead from an implanted or external electrical stimulator through a TASIF axial bore to locate one or more electrical stimulation electrode of the lead or incorporated with an elongated axial spinal implant or spinal disc implant within or between adjoining vertebral bodies to apply electrical stimulation to encourage bone growth or to counter pain in step S300; (10) extending a catheter from an implanted or external drug dispenser through a TASIF axial bore to a drug delivery port of the catheter or incorporated with an elongated axial spinal implant or spinal disc implant to dispense a drug within or between adjoining vertebral bodies or outside vertebral bodies to encourage bone growth or to counter pain in step S300; and (11) performing a brachytherapy of a vertebral body through an axial bore to treat metastatic disease in the spine or adenopathy in the retroperitoneum. The TASIF axial bore openings at the anterior or posterior sacral positions are preferably backfilled, plugged or closed following each such therapeutic procedure with a bone growth material, bone cement and/or prosthetic plug or cap.

The axial insertion of spinal implants referenced above includes the implantation of any of a wide variety of implants, some of which are described elsewhere herein. For example, implants in the form of a solid rod of either polymeric or metal construction may be utilized. Modifications to the solid rod include surface texturing, interference fit structures for engaging cancellous or cortical bone, and the like. The rods may additionally include a drug delivery capability, such that any of a variety of drugs may elute from the implant, or be released as the implant degrades in the event of a bioabsorbable implant. Either metal or polymeric rods may be provided with a variety of apertures, for facilitating bone ingrowth as is understood in the art. For example, a variety of structures are known in the art and presently implanted laterally, known as cages. A wide variety of cages may be utilized with or without modification in the context of the present invention by axial advance into the axially extending bores described herein. Such cages often include one or more central lumen, in communication with the exterior through the side wall of the cage by way of a plurality of side wall apertures. The external surface of the side wall may be provided with a helical thread, or other radially outwardly extending structure for providing mechanical interference fit with the adjacent bone.

In addition, any of the foregoing procedures may be accompanied by a visualization step. Following creation of the axial bore, a visualization device such as an endoscope may be transluminally advanced through the bore to permit inspection of the treatment zone. Direct visualization may allow observation of the health and general condition of the vertebral bodies and intervertebral discs, as well as assessment of the progress or result of a nucleus removal or full disc removal procedure. In addition, therapeutic and/or diagnostic procedures may be monitored under direct visualization through the axial bores created in accordance with the present invention.

For convenience of illustration, the therapeutic procedures are illustrated in the drawings and described as follows as being performed through an anterior percutaneous tract formed using an anterior tract sheath 96 and TASIF axial bore 152. But, it will be understood that the procedures may be performed through a posterior percutaneous tract and TASIF axial bore 22 and that certain of the procedures may be advantageously performed using parallel or diverging TASIF axial bores.

In each of the following procedures to deliver a therapy, the anterior TASIF axial bore 152 is formed, as described above, through the use of anterior tract sheath 96 (FIG. 9) inserted earlier through the presacral space 24 from a skin incision 28 to the anterior target point of the anterior surface of sacral vertebra S1 that defines the percutaneous tract 26. The shaped end 98 of the anterior tract sheath 96 is aligned with the anterior surface of the sacral vertebra S1 during step S100. The shaped end 98 may be formed with attachment teeth or threads to fix it to the sacral bone. It will be understood that the therapeutic procedures of the present invention may be performed through the lumen of such a tract sheath 96 or simply through a defined anterior tract 26 extending through the pre-sacral space 24 to axially access the vertebrae.

It will be understood that each of the following therapies to the spinal discs or the vertebral bodies can be conducted on more than one spinal disc or vertebral body or on one or more spinal disc and one or more vertebral body traversed by at least one TASIF axial bore. For example, two, or three or four or five or more spinal discs may be accessed by a single TASIF axial bore, and treated in one of the following ways, generally starting with the cephalad spinal disc. Then, the portion of the TASIF axial bore between the cephalad and caudal spinal disc may be closed by an artificial axial spinal implant or bone growth material as appropriate. The caudal spinal disc is then treated, and the portion of the TASIF axial bore between the caudal spinal disc and the anterior or posterior sacral bore entry point may then be closed by an artificial axial spinal implant or bone growth material as appropriate. Similarly, cephalad and caudal vertebral bodies may be treated by vertebroplasty or balloon-assisted vertebroplasty, and the intervertebral disc may also be treated by one of the following described therapies. For convenience, the treatment of only a single spinal disc or vertebral body is described and illustrated in the drawings.

Thus, the following exemplary therapeutic procedures of the present invention are understood to involve accessing an anterior or posterior sacral position of a sacral vertebra in alignment with the visualized, AAIFL or PAIFL extending in said axial aspect cephalad through a series of adjacent vertebral bodies of adjacent vertebrae. Then, from the accessed anterior sacral position, at least one anterior or posterior TASIF axial bore is bored in alignment (as defined herein) with the AAIFL or PAIFL axially through at least the caudal sacral vertebra and through or into one or more cephalad vertebral bodies of the series of adjacent vertebral bodies and any interposed, intervertebral, spinal discs. The delivery of the therapies is followed by the withdrawal of any tract forming tools and a simple surgical closure of the incision site. The therapies can be delivered or therapeutic procedures can be performed as follows. The procedures below are merely representative of those contemplated using the access methods of the present invention.

One simple fusion therapeutic procedure of the present invention simply involves filling the anterior or posterior TASIF axial bore(s) with a bone growth material which bridges the spinal disc and will effect bone growth across the spinal disc. The cancellous bone is typically porous with fissures and cavities, so that the bone growth material is also forced into such cancellous bone cavities and fissures. In this application, it may be desirable to bore and fill a plurality of parallel or diverging anterior or posterior TASIF axial bores to provide a number of bridges of bone growth material through the intervertebral spinal disc.

For purposes of this therapy and other fusion therapies described herein, a "bone growth material" can be one or more of the following, or any other biocompatible material judged to have the desired physiologic response, including any natural or artificial osteoconductive, osteoinductive, osteogenic, or other fusion encouraging material. Particularly, morselized cortical, cancellous, or cortico-cancellous bone graft, including autograft, allograft, or xenograft might be employed. Or any bone graft substitute or combination of bone graft substitutes, or combinations of bone graft and bone graft substitutes, or bone inducing substances, could be employed. Such bone graft substitutes or bone inducing substances include, but not limited to, hydroxyapatite, hydroxyapatite tricalcium phosphate; bone morphogenic protein (BMP) and calcified or decalcified bone derivative and resorbable bone cements. The resorbable cement material can be a calcium derivative generally composed of hydroxyapatite, orthophosphoric acid, calcium carbonate, and calcium hydroxide formed into a semi-liquid paste with an alkaline solution of sodium hydroxide and water or a composition comprising polypropylene fumarate or a mixture of calcium phosphates. Other compositions that may be employed comprise calcium salt filler, N-vinyl-2-pyrrolidone, and a peroxide or free radical initiator. The bone graft material may be mixed with a radiographic material to enable its visualization during delivery to assure proper disposition and filling of bores, cavities and spaces described herein.

In certain cases, e.g. correcting spondylolisthesis, it is necessary to realign the vertebral bodies before boring the anterior or posterior TASIF axial bore(s) and to reinforce or stabilize the vertebrae pending fusion. In this case, and in other cases where reinforcement is deemed necessary, a pre-formed elongated axial spinal implant can be inserted into at least one of the anterior or posterior TASIF axial bore(s) along with bone growth material. The axial spinal implant can be a surface roughened metal rod or porous tube of the type described in the above-referenced 620 application that is configured to the particular bore curvature and size and surface treated to bite into vertebral bone and/or to promote bone ingrowth.

This therapy provides a simple and relatively atraumatic approach to the vertebrae of interest where there is no need to treat or remove the intervertebral disc. Fusion may be effected in other ways described as follows using the bone growth materials and optionally using an elongated axial spinal implant.

As described above, the complete and partial discectomy procedures followed by introduction of fusion materials and devices conducted in the past have been done through lateral exposure of the disc that presents a number of problems that are eliminated by the present invention.

In its simplest form of this aspect of the present invention, fusion of the prepared endplates of, for example, L4 and L5 can be effected by pumping a bone growth media into the disc space 154 through the TASIF axial bore 152 and percutaneous tract 26. A catheter having a straight or flexible tip section can be employed that is extended through the axially aligned anterior tract 26 and the TASIF axial bore 152 to dispense the bone growth material in the disc space 154. A plunger can also be employed that is extended through the axially aligned anterior tract 26 and the TASIF axial bore 152 to pack the dispensed material from the TASIF axial bore 152 into the disc space 154. Then, the caudal end opening or the full length of the TASIF axial bore 152 is plugged with an artificial plug or bone growth material, and the sheath 96 is withdrawn. The incision 28 is closed and the patient rests for a time until bone growth takes place.

This procedure may suffer from the inability to adequately fill the disc space 154 or to confine the dispensed bone growth material within the disc space during the procedure and may require prolonged bed rest recuperation to avoid later settling and ejection of the bone growth material.

Figure 11:
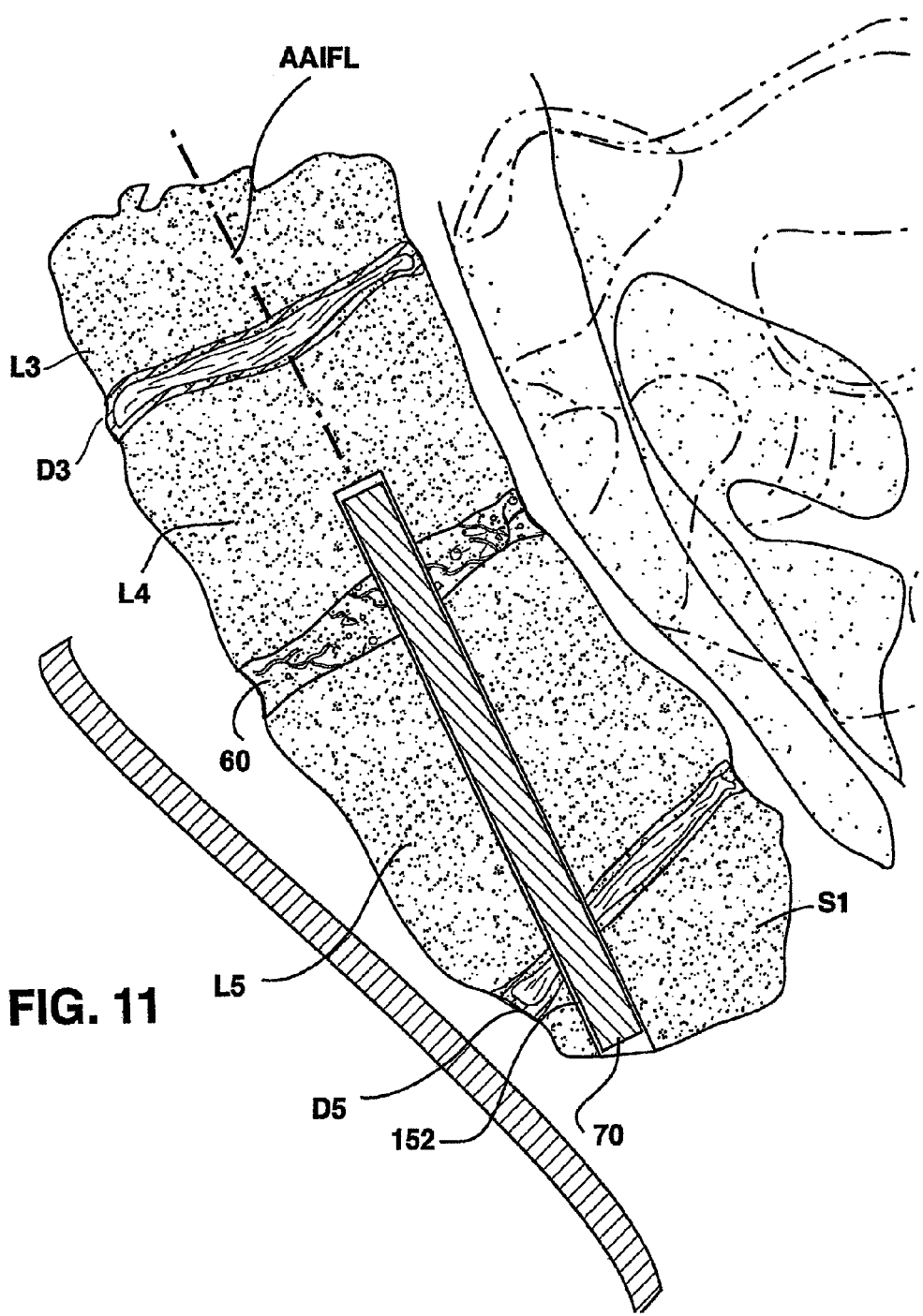
FIG. 11 illustrates, in a partial cross-section side view, one manner of strengthening the fusion of the vertebral bodies by implantation of an elongated axial spinal implant into the TASIF axial bore bridging the filled or unaugmented disc space.

A pre-formed, rod shaped, artificial axial spinal implant 70 can be inserted into the TASIF axial bore 152 to fill all or part of it in order to help maintain the distraction of the vertebral bodies as shown in FIG. 11. The pre-formed axial spinal implant 70 can extend into the cephalad vertebral body L4 if the TASIF axial bore 154 extends into it as shown in FIG. 11 and may include the distraction and shock absorbing characteristics of the particular axial spinal implants described below. In this case, it may be desirable to form parallel or diverging TASIF axial bores and implant an axial spinal implant in each bore. The pre-formed, rod shaped, artificial axial spinal implant 70 may employ a fixation mechanism and/or be fixed in place using one of the above described bone growth materials.

The spinal implant 70 can take any of a variety of forms as will be appreciated by those of skill in the art in view of the disclosure herein. For example, surface structures may be provided for enhancing bone ingrowth for resistance to axial compression or elongation following a bone ingrowth period. Any one or combination of structures such as surface texturing, helical threads, radially outwardly extending flanges or arms may be utilized to enhance the integrity of the junction. In addition, bone ingrowth may be facilitated by providing the spinal implant 70 with a central lumen extending at least part way and preferably throughout the axial length of the device. A plurality of side wall openings may also be provided, to enable communication between the adjacent bone and the interior of the spinal implant 70. A variety of structures are presently known which meet this general description, and examples may be found in U.S. Pat. No. 6,287,343 to Kuslich et al. and U.S. Pat. No. 4,501,269 to Bagby, the disclosures of which are incorporated in their entireties herein by reference. The tubular implant having perforated side walls may additionally be provided with an external helical thread, to further enhance the integrity of the resulting joint. A single spinal implant 70 or multiple spinal implants may be implanted within a treatment zone in the spine, as is discussed elsewhere herein.

Figure 11A:
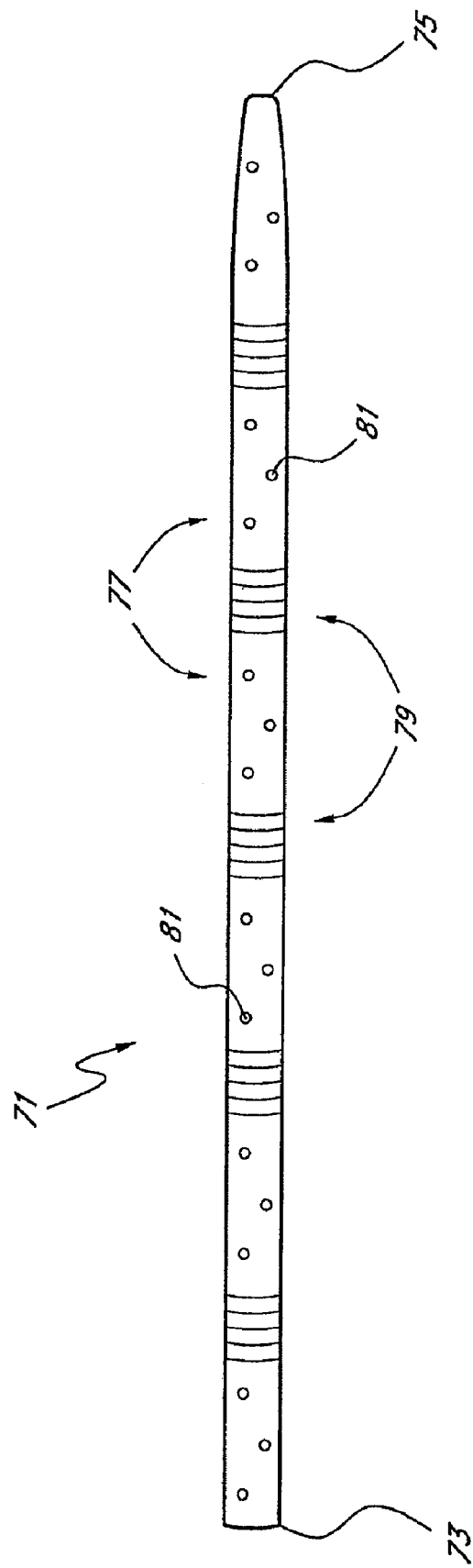
FIG. 11A illustrates, in side elevational, schematic view, an articulating axial spinal implant in accordance with the present invention.

Referring to FIG. 11a, there is illustrated an articulating spinal implant 71 in accordance with another aspect of the present invention. The articulating spinal implant may be transluminally positioned within the TASIF axial bore 152, to span two or three or four or five or more adjacent vertebral bodies. Articulating spinal implant 71 comprises generally a proximal end 73, a distal end 75 and an elongate articulated body extending therebetween. The body comprises a plurality of segments 77, (e.g. two or three or four or more) each separated by an articulation or flexible joint 79. In the implanted orientation, each segment 77 axially corresponds to a vertebral body, and each joint 79 corresponds to a disc. Thus, the axial length of each segment 77 approximates the column height of the intended corresponding vertebral body, and the axial length of each joint 79 approximates the column height of the corresponding disc.

Each segment 77 may additionally be provided with one or more anchoring and/or ingrowth surface structures to facilitate cancellous bone and/or cortical bone ingrowth, and to anchor the segment 77 within the vertebral body. In the illustrated embodiment, each segment 77 is provided with a plurality of apertures 81 to permit cancellous bone ingrowth and/or permit the expression of one or more bone growth materials. For this latter application, at least some and preferably all of the apertures 81 are in communication with a central lumen (not illustrated) which is accessible at proximal end 73 by an infusion device positioned outside of the body. One or more suitable bone growth materials, such as those discussed above, are expressed through the lumen, and out of the apertures 81 as will be understood by those of skill in the art in view of the disclosure herein. In addition to, or instead of the apertures 81, any of a wide variety of surface structures such as pitted or textured surfaces, radially outwardly extending anchors, recesses or projections may be included, to facilitate anchoring within the bone following a post procedure healing period.

The joints 79 may be formed in any of a variety of manners, such as by the provision of a bellows shaped plurality of alternating annular recesses and ridges. The material of the adjacent segments 77 may be reduced in diameter to increase lateral flexibility at a living hinge. Alternatively, a ball joint or mechanical pivot such as two arms or sidewalls connected by and rotatable about a connector such as a hinge pin, rivet or the like may be used. A metal coil spring or biocompatible compressible elastomeric materials may also be used to permit limited flex and axial compressibility depending upon the desired post implantation performance.

The articulating implant 71 may be formed in any of a variety of ways, which will be apparent to those of skill in the art. For example, all or portions of the implant 71 may be formed by molding or extrusion of any of a variety of polymeric materials well known in the medical device arts, such as PEEK, PET, nylon, PTFE, various densities of polyethylene, and the like. Alternatively, any of a variety of solid or tubular metal stock such as stainless steel, titanium or nitinol may be utilized. Hinge point 79 may be machined in, molded in or fabricated during subsequent assembly processes depending upon the hinge design. The overall dimensions of the articulating implant 71 will be selected dependent upon the intended use environment. In general, for an adult human patient, the outside diameter of the implant 71 will be within the range of from about 0.25 inches to about 1 inch. The length of the implant 71 will depend upon the number of discs and vertebral bodies which the implant 71 is intended to span.

Figure 12:
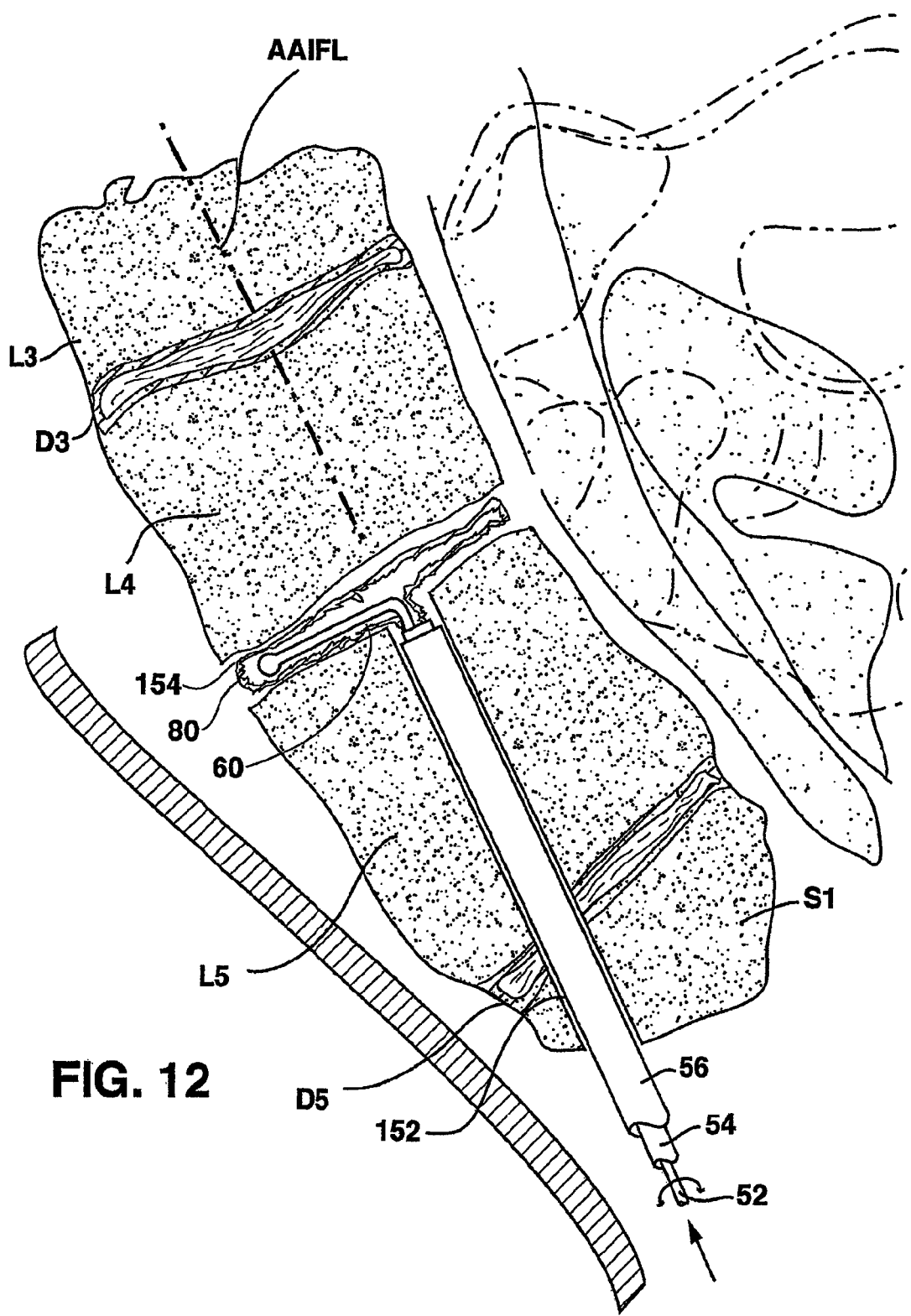
FIG. 12 illustrates, in a partial cross-section side view, one manner of implanting a spinal disc implant following discectomy of a disc effected through the delivery of a porous envelope in a deflated condition through a TASIF axial bore and into the disc space.

Alternatively, fusion of the vertebral bodies can be effected according to a further aspect of the present invention using spinal disc implants that are dispensed into the disc space through the TASIF axial bore 152 and percutaneous tract 26 and maintained there in a variety of ways. One approach, shown in FIG. 12, is to dispense a porous, deflated, shaped bag or balloon or sack or other envelope 80 of a type described in the above-referenced '679 patent into the disc space 154 and to then fill and inflate the envelope 80 with a bone growth material 60 of one of the types described above as shown in FIG. 13, and to close the opening into the envelope 80. The porous fabric has pores that are small enough to confine the bone growth material within the envelope while allowing passage of fluids and bone growth therethrough. The envelope 80 could be formed of a tightly woven, high molecular weight, high tenacity, flexible polymeric fabric e.g., high molecular weight polyethylene, polyester, polyolefine, polyethylene terephthalate, polytetrafluoroethylene polysulfone, nylons, or any other high molecular weight, and other high tenacity materials including carbon fiber yarns, ceramic fibers, metallic fibers, etc.

The envelope 80 can be inserted into the prepared disc space 154 in a variety of ways, one of which is shown in FIG. 12. The envelope 80 is folded against a blunt tip flexible push wire 52 which extends through the lumen of a fill tube 54 that extends into the balloon opening. The folded envelope 80, push wire 52 and fill tube 54 are in turn inserted into the lumen of a tubular catheter or sheath 56 that is advanced through the percutaneous tract 26 and TASIF axial bore 152. Then, the envelope 80 is advanced into the prepared, distracted disc space 154 and spread out by pushing and torqueing the push wire 52. Air or liquid inflation of the shaped envelope 80 can also be used to spread the envelope out in the disc space instead of the push wire 52.

Figure 13:
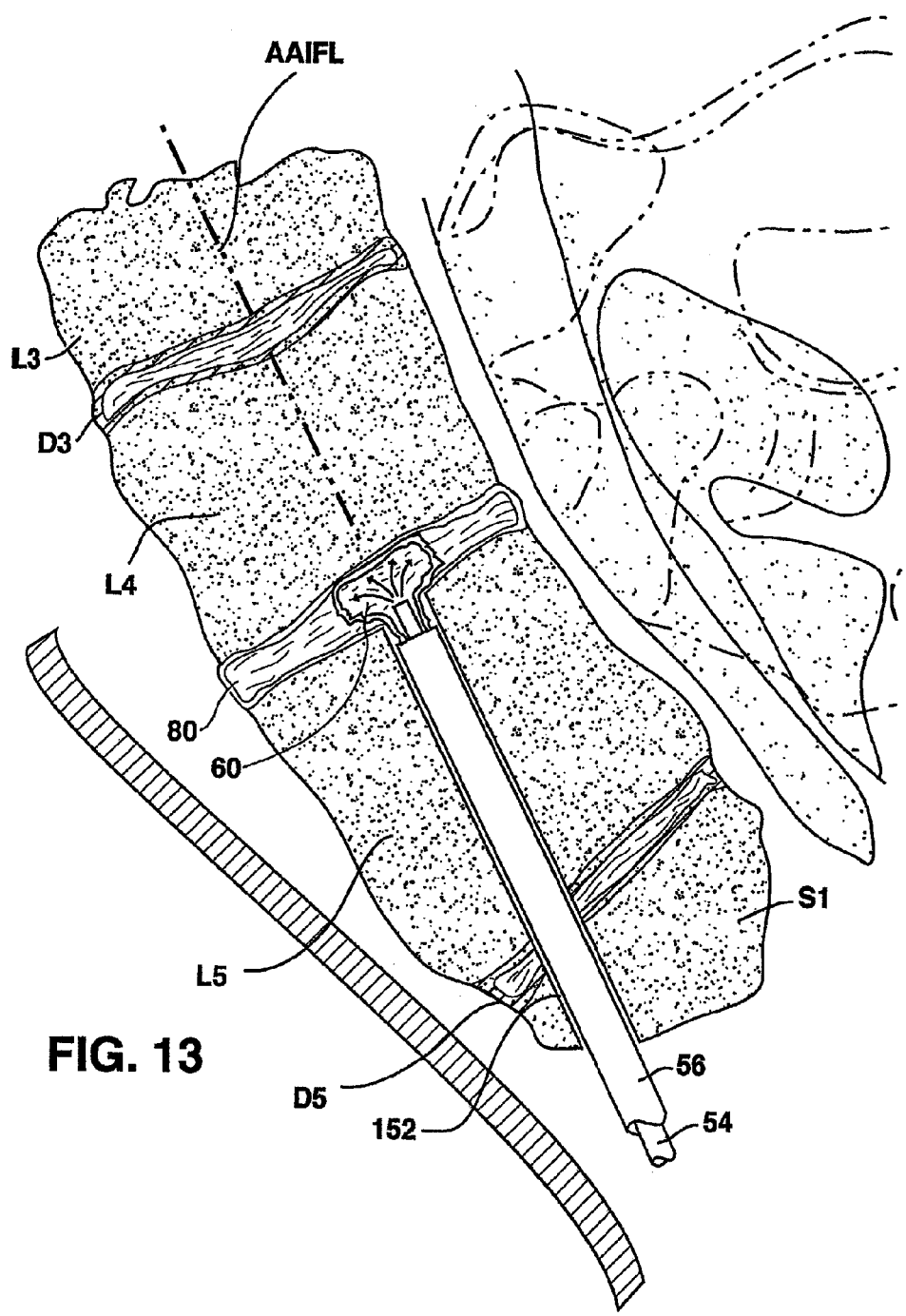
FIG. 13 illustrates the filling of the porous envelope of FIG. 12, with a bone growth material for fusion or other bio materials forming an artificial spinal disc implant.

The push wire 52 is withdrawn, air is evacuated from the envelope interior through the lumen of the fill tube 54, and bone growth material 60 is then injected through the lumen of the fill tube 54 as shown in FIG. 13. The filled envelope 80 conforms with the prepared disc space 154, and the dispensed bone growth material 60 is confined therein to maintain the spacing between the vertebral body end plates when the envelope opening is closed. The envelope opening can be closed by drawing a purse-string suture sewn around the opening tight and tying it through the TASIF axial bore 152 and percutaneous tract 26 or in other manners described in the above-referenced '679 and '736 patents and in U.S. Pat. No. 5,702,454. The bone growth material confined within the envelope 80 maintains the distraction spacing between the prepared vertebral body endplates.

One manner of maintaining the filled envelope 80 in place would be to advance an elongated axial spinal implant 70 in the caudal direction into the opening of the filled envelope 80 to abut a section of the envelope fabric against the cephalad vertebral endplate, thereby both sealing the envelope opening and locking it into place.

Another way to maintain the filled envelope 80 in place would be to form the disc space 154 with concave, prepared vertebral body endplates during the complete discectomy and to form the envelope 80 with convex sides that fit within the concave surfaces when the envelope 80 is filled with bone growth material.

As described above, the complete and partial discectomy procedures followed by a functional disc replacement implant conducted in the past have been done through lateral exposure of the disc that presents a number of problems that are eliminated by the present invention.

In this aspect of the present invention, various forms of spinal disc implants that mimic the function and characteristics of a natural disc without promoting fusion of the cephalad and caudal vertebral bodies can be inserted into the disc space through the TASIF axial bore 152 and percutaneous tract 26 and maintained there in a variety of ways. One approach is to dispense a deflated, shaped bag or balloon or sack or other envelope of a type described in the above-referenced '326 and '454 patents and in U.S. Pat. Nos. 5,888,220 and 5,562,736 into the disc space 154. Then, the envelope 80 is filled and inflated with a curable biomaterial that does not necessarily encourage bone growth and preferably is resilient. The '326, '220 and '736 patents describe performing a discectomy through lateral approaches to remove the nucleus while retaining as much of the annulus as possible, given the lateral penetration through it. In accordance with this aspect of the present invention, the annulus is removed in the complete discectomy described above, and the deflated envelope 80 is inserted and inflated through the TASIF axial bore 152 and percutaneous tract 26 as shown in FIG. 12 and described above. The envelope 80 conforms with the prepared disc space, and the dispensed biomaterial is confined therein to maintain the spacing between the vertebral body end plates when the envelope opening is closed. The dispensed biomaterial confined within the envelope maintains the distraction spacing between the prepared vertebral body endplates but does not necessarily encourage fusion.

In this case, the biomaterial filling the envelope 80 is a material that is capable of being introduced to the site of a joint by minimally invasive means, and be hydrated or cured in place to provide desired physical-chemical properties as described, for example, in the above-referenced '326, '454, '220 and '736 patents. A hydrogel can be injected into the envelope 80 in a liquid or dry particulate form or in microspheres or beads in the manner shown in FIG. 13. A preferred hydrogel is formulated as a mixture of hydrogel polyacrylonitrile or any hydrophilic acrylate derivative with a unique multiblock copolymer structure or any other hydrogel material having the ability to imbibe and expel fluids while maintaining its structure under various stresses. For example, the hydrogel can be formulated as a mixture of polyvinyl alcohol and water. The hydrogel core formed within the envelope 80 will swell as it absorbs fluids through the porous fabric wall of the envelope 80 much like a native nucleus. The hydrogel core has a time constant of swelling which is highly similar to that of the natural nucleus and will thus experience a 5-30% and preferably a 15-20% volume change depending on load over the course of 2-8 (preferably 4-8) hours. When fully hydrated, the hydrogel core will have a water content of between 25-65%. The hydrogel material of the preferred embodiment is manufactured under the trade name Hypan® by Hymedix International, Inc. In addition, any of the hydrogels and solvents identified in the above-referenced '326 patent may be employed to fill the envelope 80.

The preferred woven construction of the envelope creates a plurality of small openings large enough to allow bodily fluids to interact with the hydrogel core, but small enough to prevent the hydrogel from escaping. Preferably, the openings have an average diameter of about 10 micrometers, although other dimensions are acceptable. While the fabric is described as woven, any other configuration having a semi-permeable or porous attribute can be used. The flexible material allows expansion and contraction of the hydrogel core in a controlled fashion as it imbibes and expels fluids. The hydrogel core acts as a cushion against various loads placed upon it. The hydrogel core imbibes surrounding fluids and expands as the load is decreased (e.g. when the patient reclines). To help achieve this effect, the preferred envelope fabric is substantially inelastic and has a burst strength which is greater than the swelling pressure of the hydrogel core when fully hydrated to prevent rending and loss of the hydrogel core. Suitable envelope materials include This therapeutic procedure of the present invention provides a shock absorbing functional disc replacement of the nucleus of the spinal disc and can be advantageously conducted without any injury to any ligaments, muscles and facet joints of the spinal motion segment. Depending upon the physical properties of the nucleus augmentation or replacement media, the outer envelope may be omitted and the media injected or placed directly in the nucleus space. Advantageously, the present invention leaves the annulus fibrosis intact.

In addition, it is also possible to augment a spinal disc by introducing one or more artificial spinal disc implant or other biomaterials to provide a functional disc replacement implant or bone growth materials to effect fusion into the void or cavity that is made within the annulus AF, thereby employing the annulus AF to retain the introduced implants or biomaterials or fusion enhancing materials in place. The annulus AF can itself be used as an envelope to contain the delivered disc augmentation materials comprising spinal disc implant(s), bone growth material or other biomaterials. Optionally, means are provided to contain the disc augmentation materials within the desired space, e.g., by delivering the disc augmentation materials into an additional envelope within the cavity. To effect fusion, the TASIF axial bore 152 may be extended into the cephalad vertebral body and axial spinal implants and/or bone growth material dispensed within the cavity and the TASIF axial bore 152. Or a portion of the caudal and cephalad cartilaginous endplates and vertebral body endplates can be removed in the partial discectomy to expose vertebral bone to promote fusion with the bone growth materials dispensed into the cavity.

As described above, the vertebroplasty procedure involves forcing vertebral body repairing or reinforcing material comprising bone growth material or bone cement for repairing or reinforcing the vertebral body into the cancellous bone of the fractured vertebral body. In the past, vertebroplasty has been done through a lateral exposure and penetration of the cortical bone of a side surface of the vertebral body. As noted above, the lateral approach presents a number of problems that are eliminated by the present invention.

One approach to performing a vertebroplasty in accordance with the present invention is to simply bore one or more small diameter TASIF axial bore into the fractured cancellous bone, introduce a catheter into the TASIF axial bore, and to pump in the bone growth material or bone cement so that it penetrates and fills the fissures in the cancellous bone. Then, the caudal end of the TASIF axial bore is closed where it passes through the harder cortical bone forming the caudal vertebral endplate, e.g., by use of a threaded plug as described above. This procedure may be repeated at several different angles.

Figure 14:
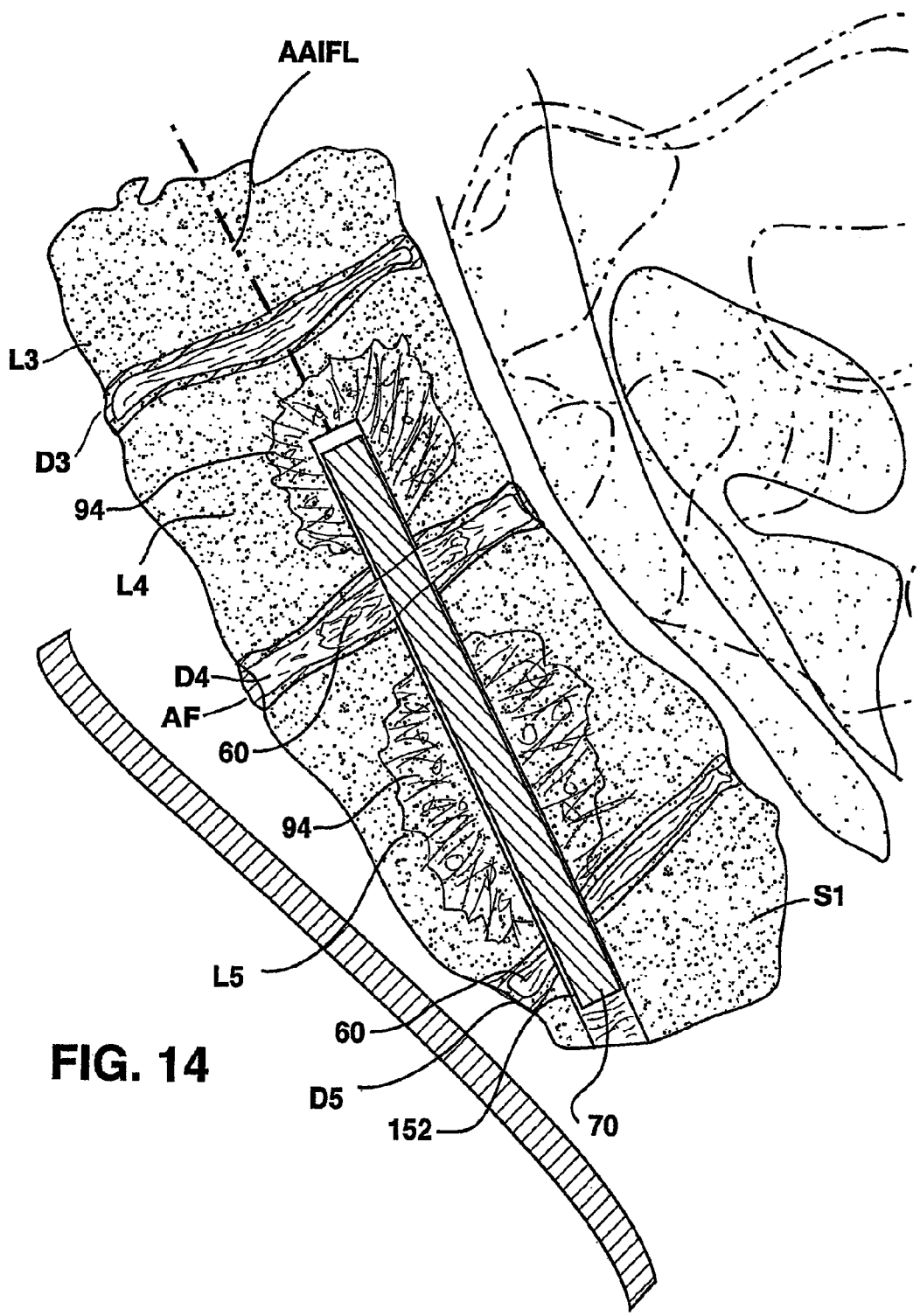
FIG. 14 illustrates, in a partial cross-section side view, a combination of above described therapies comprising the injection of bone growth materials or bone cement through an axial bore into cancellous bone of two vertebral bodies and intervertebral disc cavities before or after or simultaneously with insertion of an elongated axial spinal implant into the axial bore to effect a fusion with reinforcement of the vertebral bodies.

The above-described therapies can be combined to treat a given patient. FIG. 14 illustrates, in a partial cross-section side view, a combination of certain of the above described therapies particularly for effecting spinal fusion, and alignment, and reinforcement. In this illustrated combined therapy, the anterior TASIF axial bore 152 is formed as described above via the tract sheath 96 extending through vertebral bodies S1, L5 and into L4. Partial discectomies are performed of the intervertebral discs D5 and D4 to form respective disc cavities. A bolus of bone growth material or bone cement 60 is injected into the disc cavities of intervertebral discs D4 and D5 through the axial bore. Vertebroplasty procedures are then performed to inject a bone growth material or bone cement mass 94 into the gaps and fissures of cancellous bone of the two vertebral bodies L4 and L5, which may or may not be fractured or collapsed. An elongated axial spinal implant 70 or 71 is inserted into the axial bore 152 and through the injected bone growth material or bone cement 94 and 60 to effect a fusion with reinforcement of the vertebral bodies L4 and L5.

In this case, the elongated axial spinal implant 70 may be a 4.0 mm by 60.0 mm carbon fiber rod having a spiral screw thread or other affixation mechanism extending along its length. This therapy may advantageously be performed using three such elongated axial spinal implants implanted in this way into three diverging axial bores to maximize the strength of the fusion.

Figure 18:
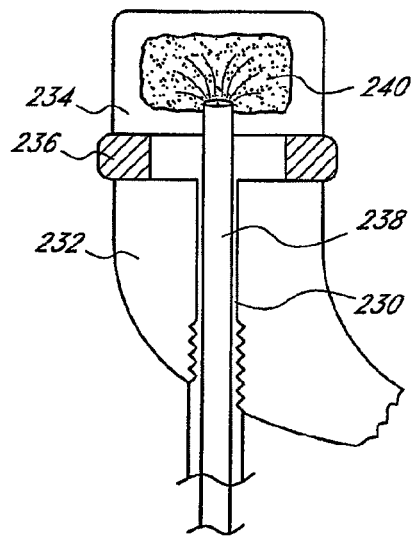
FIG. 18 is a side elevational schematic cross-section of an augmentation media infusion device injecting augmentation media into a vertebral body.
Figure 19:
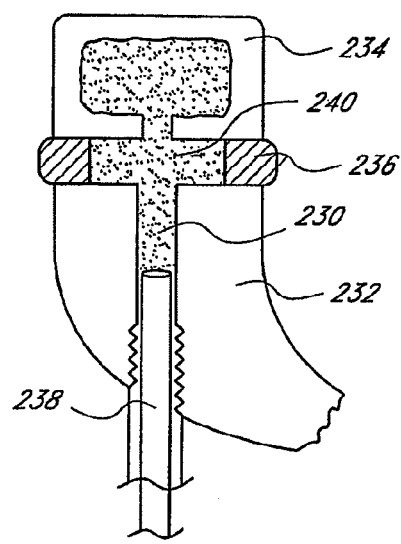
FIG. 19 is a schematic side elevational cross-section as in FIG. 18, with the augmentation catheter proximally retracted and media infused into both the vertebral body and disc space.

Referring to FIG. 15, there is illustrated a spinal augmentation catheter 200 for augmenting the vertebral bodies and/or the nucleus. The spinal augmentation catheter 200 may be advanced along any of the axial bores described previously herein. In general, the spinal augmentation catheter 200 is adapted to express a first media for treating and/or augmenting a vertebral body, as well as a second, distinct media for treating and/or augmenting the nucleus. Alternatively a single lumen augmentation catheter such as illustrated in FIGS. 18 and 19, below, can be used.

The spinal augmentation catheter 200 comprises an elongate rigid or flexible tubular body 206 extending between a proximal end 202 and a distal end 204. The body 206 may be manufactured in any of a variety of manners known in the catheter arts, such as by extrusion of suitable polymeric materials. These include, for example, PEEK, PET, various densities of polyethylene, nylon, PTFE and others known in the art. Alternatively, for relatively short axial tract length treatments, the tubular body 206 may be made from a metal such as stainless steel or nitinol. Stainless steel, nitinol and other metals may also be utilized in thin walled, flexible embodiments, as will be appreciated by those of skill in the art in view of the disclosure herein.

The tubular body 206 preferably has a diameter which is sufficiently small to permit passage through the TASIF axial bore, and have a sufficiently large interior cross-section to permit flow of the spinal augmentation media. In general, the outside diameter of catheter body 206 is often greater than about 0.25 inches and less than about 0.75 inches. The axial length of the tubular body 206 will vary depending upon the length of the treatment zone and the distance from the access site to the treatment zone.

The proximal end 202 of tubular body 206 is provided with a manifold 208 as is known in the art. Manifold 208 is further provided with a first port 210 for communicating with a first lumen 214 and, in the illustrated dual lumen embodiment, a second port 212 for communicating with a second lumen 216. First and second ports 210 and 212 may be provided with any of a variety of conventional fittings, such as luer connectors or others known in the art. Proximal manifold 208 may be injection molded, or formed in other conventional manners.

Proximal manifold 208 may be provided with additional access ports for communicating with additional lumen, depending upon the desired functionality of the device. For example, an additional lumen may be desired to infuse any of a variety of fluids, medications, contrast media for assisting visualization, aspiration or venting functions.

First lumen 214 extends throughout the length of the tubular body 206 from the proximal port 210 to a distal opening 218. In the illustrated embodiment, distal opening 218 is positioned on the distal end of the catheter 200. Alternatively, lumen 214 may be provided with one or more laterally opening ports, depending upon the desired performance characteristics.

The second lumen 216 extends between the proximal port 212 and a second distal opening 220. The second distal opening 220 is illustrated as a lateral opening on a sidewall of the catheter, spaced apart from the first opening 218.

In the illustrated embodiment, the first opening 218 is spaced axially apart from the second opening 220 by a distance which enables the first opening 218 to express media into the vertebral body while the second opening 220 is positioned within the annulus fibrosa. This construction enables augmentation of both the vertebral body and the nucleus without the necessity of moving the catheter. Following expression of media into the nucleus and vertebral body, the catheter 200 may be proximally retracted to position the first opening 218 within the next adjacent vertebral body, for augmentation of the next vertebral body—nucleus pair. Any of a variety of augmentation media may be utilized for the vertebral body and the nucleus, as has been discussed elsewhere herein.

Additional apertures may be provided along the length of the catheter body 206, such that at least two nucleus augmentations may be simultaneously accomplished and/or at least two vertebral body augmentations may be simultaneously accomplished. For example, two or three or more apertures in communication with the first lumen 214 may be spaced apart along the length of the catheter 200, alternating with two or three or more apertures in communication with the second lumen 216. In this manner, a plurality of discs and vertebral bodies may be augmented for a single axial position of the catheter 200. Following augmentation in the foregoing manner, the catheter 200 may be proximally retracted from the patient, with or without leaving a stream of augmentation media such as by way of the first aperture 218, to fill the tract left by the catheter 200.

Alternatively, the catheter 200 may be severed or disconnected below or about the point where it exists the spine, and left in place as a permanent implant. This can assist in maintaining the vertebral body and disc augmentation medias in place and provide additional support for the treated area. In an embodiment of the catheter 200 intended for permanent implantation, the detachable component of the catheter 200 may be similar to the implant 70 (FIG. 11) having one or more axially extending central lumen, in communication with the exterior through a plurality of ports. The implantable portion of the catheter 200 may be rigid such as the implant 70, or may be articulated such as the implant 71 (FIG. 11A). It may alternatively be flexible throughout its axial length. The implantable portion of a catheter 200 may also be provided with any of a variety of additional features discussed in connection with implant 70 or 71, such as cancellous and/or cortical bone ingrowth surface structures, joints 79 and/or compressible shock absorbing cushions for aligning with the discs in the implanted orientation.

In all of the above-described procedures, the visualization of the spine and the introduction of instruments employed to form the anterior or posterior axial bore(s) or lumen(s) or to perform therapies, and any spinal disc implants or axial spinal implants or other implanted medical devices is effected employing conventional imaging techniques including open MRI, fluoroscopy or ultrasound through the patient's body or using endoscopic techniques through an axial bore. Internal visualization may also be desirable in any of the procedures disclosed herein. This may be accomplished by advancing a viewing instrument such as an endoscope into the formed bore to view the walls of the bore and/or condition of the nucleus or nucleus space prior to or during the therapeutic or diagnostic procedure.

The various methods of accessing and treating the spine, using, for example, the devices disclosed herein are summarized below. The method steps may be substituted and recombined, as will be apparent to those of skill in the art in view of the disclosure herein, depending upon the desired access pathway and treatment or other procedure. All patents and other publications identified above are incorporated in their entireties herein by reference.

Certain combined therapies are further discussed in connection with FIGS. 18 through 22. Referring to FIG. 18, there is schematically illustrated a first vertebral body 232 separated from a second vertebral body 234 by a disc 236. An axial bore 230 extends through the first vertebral body 232, the disc 236 and at least into and optionally beyond the second vertebral body 234. An infusion catheter 238 is illustrated positioned within the axial bore 230, for infusing a media 240 therein as has been discussed. The nucleus has been substantially removed, with the annulus fibrosis remaining intact.

FIG. 19 illustrates the same view as in FIG. 18, with the catheter 238 proximally retracted. At this point, media 240 has been infused into both the second vertebral body 234 as well as the disc space and into the first vertebral body 232.

Figure 20:
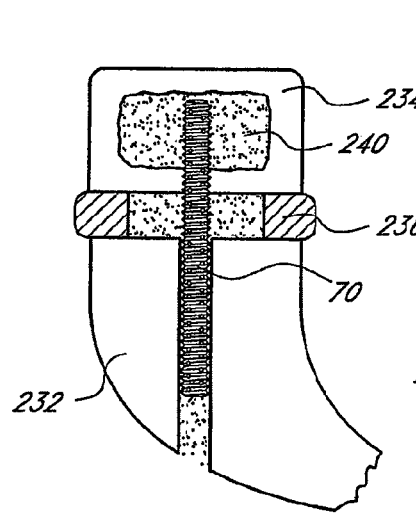
FIG. 20 is a schematic side elevational view of a fusion implant positioned axially across a disc space and into a cephalad and caudad vertebral body.

Before, after or during infusion of media into the spine, an axial spinal implant 70 may be inserted as illustrated in FIG. 20. In the illustrated embodiment, the axial spinal implant 70 comprises a proximal end 242, a distal end 244 and a tubular body 246 extending therebetween. See FIG. 22. An axially extending lumen 248 extends throughout the length of the implant 70. A plurality of apertures 250 through the side wall communicate with the central lumen 248. An external thread 251 is also provided. The proximal end 242 is provided with a releasable connector 252, for releasable connection to a complementary connector 256 on a deployment device 254.

The connectors 252 and 256 may comprise any of a variety of complementary releasable connectors, which allow insertion of the implant 70 transaxially into the treatment position in the spine, and subsequent release from the deployment device 254. In the illustrated embodiment, the releasable connector system comprises a threaded aperture on the implant 70 for threadably engaging a threaded shaft on the distal end of the deployment catheter 254. The connectors and deployment catheter may be cannulated, to permit infusion of bone growth material into the central lumen 248 from which it is expressed laterally through the apertures 250.

Figure 21:
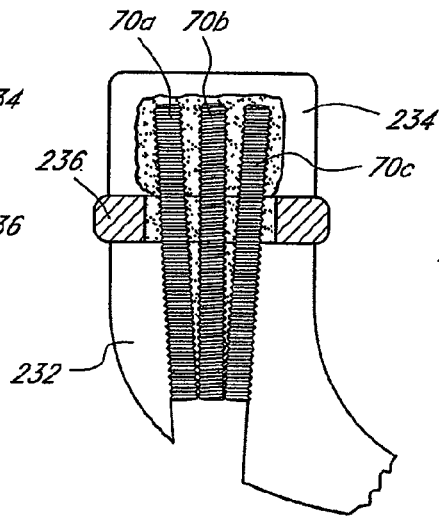
FIG. 21 is a schematic side elevational cross-sectional view of three fusion implants positioned across a disc space.
Figure 22:
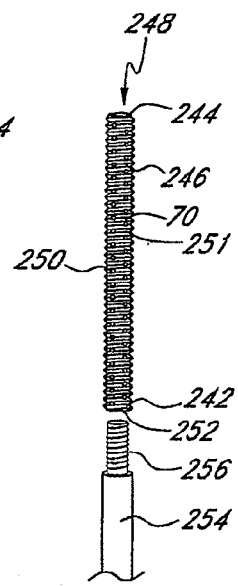
FIG. 22 is a side elevational view of a fusion implant, together with the distal end of a deployment tool.

One or two or three or four or more implants 70 may be inserted at a given level within the spine, depending upon the configuration and dimensions of the implant, and desired clinical performance. Referring to FIG. 21, three implants 70 are illustrated, each extending axially through a unique bore. The use of two or three or more implants 70 in this manner provides stability against rotation about the axis of any one of the implants 70. The implants may extend generally parallel to each other, or, as illustrated, diverge distally (cephalad) thereby enabling the use of a single introduction tract through which to introduce each of the implants 70. Alternatively, a plurality of axially elongate implants may be introduced into a single axial bore, to construct an implant in situ which is larger in cross-section than the inside diameter of the access tract. These implants may be in the form of hollow or solid rods, having external threads and optionally other features disclosed above.

In one procedure illustrated schematically in FIGS. 18 through 21, the catheter 238 is utilized to introduce BMP into the L5 body and the access tract and disc cavity. The injection catheter comprises an elongate tubular polymeric body having an outside diameter on the order of about 4 mm, to fit through the introduction sheath. The implant 70 may be in the form of a threaded solid rod or tube, or a microporous carbon fiber rod having, e.g., a 4 mm outside diameter cross-section. Rods on the order of 4 mm diameter by 60 mm length may be utilized, although a wide variety of alternate dimensions may be utilized depending upon the intended clinical performance and characteristics.

Thus, in accordance with one aspect of the present invention, there is provided a method of treating the spine. The method comprises the steps of identifying a site on the anterior surface of the sacrum, and forming a lumen from the site through the sacrum, through a disc and into at least one vertebrae. The site may be on the anterior side of the S2 or S1 vertebrae to accomplish, for example, anterior lumbar sacral fixations. A procedure is thereafter performed using the lumen. The procedure may be any of the diagnostic or therapeutic procedures identified above. In general, the procedure may comprise removing all or part of a nucleus, inserting a fixation device, or inserting a prosthetic nucleus. A bone growth facilitator may also be introduced. The lumen may extend at least as far as the L5 or L4 vertebrae, in lumbar sacral fixations, and further cephalad to or through any of the L3, L2, L1 or beyond. In one embodiment, the lumen is substantially linear, and the forming step may comprise drilling. The lumen may alternatively be formed into at least one disc, such as to enable a simple percutaneous discectomy.

In accordance with another aspect of the present invention, there is provided a method which comprises the steps of identifying a site on the posterior side of the sacrum, such as on the posterior side of S2, and forming a nonlinear lumen from the site through S2 and S1, through at least the disc at D5 and through at least one lumbar vertebrae (e.g. L5). A procedure is then performed using the lumen. The procedure may be either a diagnostic procedure or a therapeutic procedure as discussed above. The lumen may extend at least as far as the L4 vertebrae, and optionally through any or each of L4, L3, L2, L1 or beyond.

In accordance with a further aspect of the present invention, there is provided a method which comprises the steps of identifying a site on the skin of a patient, within about 10 cm from the coccyx. An access pathway is provided at the site and through tissue to the sacrum. The access pathway may include a minimally invasive puncture and/or a small surgical incision, or an open surgical cut down, although minimally invasive access is generally preferred. A lumen is created through the sacrum and at least one lumbar vertebrae. The lumen is thereafter used to perform a procedure. In particular embodiments, the site on the skin of a patient is within about 5 cm, or within about 2.5 cm from the coccyx. The lumen is generally at least about 5 cm in length, and, in some applications, is at least about 10 cm in length. The lumen may be either linear, or curved. Generally, the lumen will extend through S1 and L5, and may also extend through S2. Depending upon the desired treatment zone or site, the lumen may extend at least as far as each of L4, L3, L2, L1 or beyond.

In accordance with another aspect of the present invention, there is provided a method of treating the spine at a treatment site which is spaced apart from an access site, to minimize disruption of tissue surrounding the treatment site. The method comprises the steps of identifying an access site on the spine, and advancing a device through the access site and into the spine. The device is further advanced axially through the spine either inferiorly or superiorly for a distance across a treatment zone. The spine is treated at least in or adjacent the treatment zone, and the distance is at least about 3 cm or at least about 5 cm. In some applications, the distance is at least about 7 cm or 10 cm or 15 cm or greater. The access site may be on the sacrum, on the lumbar, thoracic or cervical portions of the spine. In general, the treatment zone may include or extend beyond the second or third or fourth or fifth vertebrae in either the inferior or superior direction from the vertebrae which includes the access site.

The method may further comprise the step of introducing the device percutaneously through the skin prior to the advancing step, such as through a tissue pathway having a cross section no greater than about 2 cm or no greater than about 1.5 cm or 1.0 cm or less. In certain applications, the tissue pathway is within the range of from about 0.35 cm to about 0.5 cm in cross section. The further advancing step may comprise advancing the device along a linear path through the spine, typically in an anterior approach. Alternatively, the advancing step may comprise advancing the device along a non-linear path through the spine, such as in a posterior approach to an access point on S2, or in any approach (anterior, posterior or lateral) to the spine in any of the lumbar, thoracic or cervical portions of the spine. The treating step may comprise implanting one or more fixation devices or any of the therapeutic or diagnostic procedures discussed elsewhere herein.

In accordance with a further aspect of the present invention, there is provided a method of treating the spine. The method comprises the steps of creating a minimally invasive passageway through tissue and into the spine, wherein the passageway has a longitudinal axis and a length of at least about five times its average width. The method additionally comprises the step of introducing at least one device through the passageway to treat the spine, wherein an extension of the axis extends through at least two intervertebral discs. In certain applications, the passageway has a length of at least about ten times its average width. The passageway may pass through the skin within about 10 cm, and in some procedures within about 5 cm of the coccyx. In certain embodiments, the passageway enters the spine on the anterior side. Alternatively, the passageway may enter the spine on the posterior side.

In accordance with another aspect of the present invention, there is provided a method of performing a procedure from the inside of the spine, while minimizing the cross-sectional area of an access pathway to the procedure site. The method comprises the steps of advancing a device through an access pathway in the spine to a procedure site, while the device has a first, reduced crossing profile. The pathway may have a length within the spine of at least about 3 cm or 5 cm, or as much as 10 cm or 15 cm or greater, depending upon the desired access site and treatment zone. In general, the length of the pathway is sufficient to displace the procedure injury due to the access from the diseased or injured hard (i.e. bone) or soft tissue at the treatment site. The crossing profile of at least a portion of the device is enlarged at the treatment site to perform the procedure. The advancing step comprises advancing the device through at least one vertebrae and at least one disc. The enlarging step may comprise advancing or inclining at least a portion of the device radially outwardly from a longitudinal axis of the device, to perform the procedure. The procedure may include any of those identified elsewhere herein, including removing a portion of or all of the nucleus and/or implanting material into the spine.

In accordance with another aspect of the present invention, there is provided a method of fusing the spine. The method comprises the steps of identifying a site on the anterior surface of the sacrum. A lumen is formed from the site through the sacrum, through a disc, and into at least one vertebrae, and optionally through at least a second or third or fourth vertebrae. A fusion implant is introduced through the lumen. In one application, the introducing step comprises introducing an elongate metal fusion device. Alternatively, the introducing step comprises introducing a bone growth stimulating or facilitating material or a cure in place media.

In accordance with a further aspect of the present invention, there is provided a method of accessing the spine through a site on the anterior of the sacrum. The method comprises the steps of introducing an access device through a tissue tract from the surface of the skin to a first site on the anterior of the sacrum. The access device is advanced cephalad along the anterior surface of the sacrum to a second site. The sacrum is entered at the second site. The first site may be inferior to the S2, such as on one of the coccygeal vertebrae.

In one application, the advancing step comprises advancing the distal end of the access device, both distally and laterally, as the distal end moves along the concavely curved anterior surface of the spine, such as the coccygeal vertebrae or sacrum. This allows creation of a linear access pathway from the access point on the skin to the S2 or S1, without damaging internal structures such as the bowel which are pushed out of the way. The introducing step may comprise introducing a blunt needle trocar to allow the device to sweep along the spine while minimizing trauma to the spine or adjacent tissue. The introducing step may comprise introducing the access device through the paracoccygeal space. The second site may be on or cephalad to S2.

The method may additionally comprise a step of positioning a guide such as a wire or a tubular sheath through the tissue tract to the second site. A fixation device may be introduced along the wire or through the sheath. In one application, the fixation device is positioned across at least the S1 and L5 vertebrae. The fixation device may be positioned across at least the S1, L5 and L4 vertebrae, and optionally into the L3 vertebrae.

In accordance with yet a further aspect of the present invention, there is provided a method of positioning an access guide such as a sheath from a paracoccygeal entrance point to the S2 vertebrae. The method comprises the steps of introducing an access device through tissue in the paracoccygeal space. A distal end of the access device is advanced into contact with the sacrum. The distal end is swept along the curved anterior surface of the sacrum towards the S2 vertebrae, thereby displacing anatomical structures such as the bowel from the path of the access device. The distal end of the access device is then fixed with respect to the S2 vertebrae. The access device may be substantially linear or curved The advancing step may comprise advancing the sheath through an incision. Alternatively, the advancing step may comprise advancing the sheath through a puncture. The fixing step may comprise threadably engaging the distal end of the sheath in an aperture in the S2, or driving a penetrating distal anchor into the bone at the fixation site.

While the present invention has been illustrated and described with particularity in terms of preferred embodiments, it should be understood that no limitation of the scope of the invention is intended thereby. Features of any of the foregoing methods and devices may be substituted or added into the others, as will be apparent to those of skill in the art. The scope of the invention is defined only by the claims appended hereto. It should also be understood that variations of the particular embodiments described herein incorporating the principles of the present invention will occur to those of ordinary skill in the art and yet be within the scope of the appended claims.

What is claimed is:

1. A method of augmenting the spine, comprising the steps of:
   providing an elongate catheter, having a proximal end, a distal end, and at least one lumen extending at least partially therethrough;
   advancing the distal end of the catheter in a cephalad direction substantially axially with respect to the spine at least partially through at least a portion of a previously created bore in the anterior surface of at least one vertebral body, the bore in fluid communication with at least one disc;
   expressing at least a first media from the catheter into the spine; and
   removing the catheter from the spine.

2. A method of augmenting the spine as in claim 1, wherein the advancing step comprises advancing the distal end through at least one vertebral body.

3. A method of augmenting the spine as in claim 1, wherein the first media comprises a nucleus augmentation material.

4. A method of augmenting the spine as in claim 1, wherein the expressing step comprises delivering electricity.

5. A method of augmenting the spine as in claim 1, further comprising the step of introducing a spinal fusion cage axially into the spine.

6. A method of augmenting the spine as in claim 1, wherein the advancing step comprises advancing the catheter through an artificial lumen created axially through the spine.

7. A method of augmenting the spine as in claim 6, further comprising the step of forming the lumen prior to the advancing step.

8. A method of augmenting the spine as in claim 6, further comprising the step of forming the lumen simultaneously with the advancing step.

9. A method of augmenting the spine as in claim 8, wherein the providing step comprises providing a catheter having a cutting tip on the distal end.

10. A method of treating the spine, comprising the steps of:
    advancing a distal end of a device through an access site on the anterior surface of the spine and into the spine;
    further advancing the device in a cephalad direction substantially axially with respect to the spine and at least partially across a treatment zone;
    expressing a material from the device within the treatment zone; and
    releasing at least a portion of the device within the spine.

11. A method of treating the spine as in claim 10, wherein the access site is on the sacrum.

12. A method of treating the spine as in claim 10, wherein the access site is on the lumbar spine.

13. A method of treating the spine as in claim 10, wherein the access site is on the thoracic spine.

14. A method of treating the spine as in claim 10, wherein the further advancing step comprises advancing the device along a linear path through the spine.

15. A method of treating the spine as in claim 10, wherein the expressing step comprises expressing the material into a nucleus of a disk.

16. A method of treating the spine as in claim 10, wherein the material is a bone growth material.

17. A method of treating the spine as in claim 10, wherein the material is a bone cement.

* * * * *

UNITED STATES PATENT AND TRADEMARK OFFICE
CERTIFICATE OF CORRECTION

PATENT NO. : 7,744,599 B2
APPLICATION NO. : 11/762669
DATED : June 29, 2010
INVENTOR(S) : Andrew H. Cragg It is certified that error appears in the above-identified patent and that said Letters Patent is hereby corrected as shown below:

In Column 2, Page 4 (Item 56), Line 60, under Other Publications, change "ofSpinal" to --of Spinal--.

In Column 2, Page 5 (Item 56), Line 12, under Other Publications, change "Phneumography" to --Pneumography--.

In Column 2, Line 21, change "micropolysacharides" to --micropolysaccharides--.

In Column 4, Line 66, change "laparascopic" to --laparoscopic--.

In Column 5, Line 24, change "artiroscopic" to --arthroscopic--.

In Column 5, Line 63, change "posteriolateral" to --posterolateral--.

In Column 20, Line 22, change "620" to --'620--.

In Column 22, Line 43, change "polytetrafluoroethylene" to --polytetrafluoroethylene,--.

In Column 31, Line 4, change "curved" to --curved.--.

Signed and Sealed this

Twenty-first Day of December, 2010

David J. Kappos
*Director of the United States Patent and Trademark Office*